United States Patent
Rieth et al.

(10) Patent No.: US 9,539,193 B2
(45) Date of Patent: Jan. 10, 2017

(54) ALKYL KETAL ESTERS AS DISPERSANTS AND SLIP AGENTS FOR PARTICULATE SOLIDS, METHODS OF MANUFACTURE, AND USES THEREOF

(75) Inventors: Lee Richard Rieth, Plymouth, MN (US); Dorie J. Yontz, Bloomington, MN (US); Nicholas Morante, Holbrook, NY (US)

(73) Assignee: GFBIOCHEMICALS LIMITED, Valletta (MT)

( * ) Notice: Subject to any disclaimer, the term of this patent is extended or adjusted under 35 U.S.C. 154(b) by 1055 days.

(21) Appl. No.: 13/104,823

(22) Filed: May 10, 2011

(65) Prior Publication Data

US 2011/0274634 A1 Nov. 10, 2011

Related U.S. Application Data

(60) Provisional application No. 61/332,982, filed on May 10, 2010, provisional application No. 61/332,978, filed on May 10, 2010.

(51) Int. Cl.

| | |
|---|---|
| *A61K 8/92* | (2006.01) |
| *A61K 8/49* | (2006.01) |
| *A61K 8/25* | (2006.01) |
| *A61K 8/29* | (2006.01) |
| *A61K 8/31* | (2006.01) |
| *A61Q 1/04* | (2006.01) |
| *A61Q 1/10* | (2006.01) |
| *A61Q 1/12* | (2006.01) |
| *A61Q 3/00* | (2006.01) |
| *A61Q 1/02* | (2006.01) |
| *A61Q 1/06* | (2006.01) |
| *C09D 7/12* | (2006.01) |
| *A01N 25/00* | (2006.01) |
| *A61K 8/34* | (2006.01) |
| *A61K 8/35* | (2006.01) |
| *A61K 8/368* | (2006.01) |
| *A61K 8/97* | (2006.01) |
| *A61K 47/22* | (2006.01) |
| *A61Q 5/10* | (2006.01) |

(Continued)

(52) U.S. Cl.
CPC ............ *A61K 8/498* (2013.01); *A01N 25/00* (2013.01); *A61K 8/25* (2013.01); *A61K 8/29* (2013.01); *A61K 8/31* (2013.01); *A61K 8/34* (2013.01); *A61K 8/35* (2013.01); *A61K 8/368* (2013.01); *A61K 8/4953* (2013.01); *A61K 8/4973* (2013.01); *A61K 8/922* (2013.01); *A61K 8/925* (2013.01); *A61K 8/927* (2013.01); *A61K 8/97* (2013.01); *A61K 47/22* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 3/00* (2013.01); *A61Q 5/10* (2013.01); *A61Q 9/04* (2013.01); *A61Q 15/00* (2013.01); *A61Q 17/04* (2013.01); *C09D 7/1233* (2013.01); *A61K 2800/49* (2013.01); *C08K 5/156* (2013.01)

(58) Field of Classification Search
CPC ............ A61K 8/498; A61K 8/25; A61K 8/29; A61K 8/31; A61K 8/4973; A61K 8/922; A61K 8/925; A61K 8/927; A61K 8/34; A61K 8/35; A61Q 1/04; A61Q 1/10; A61Q 1/12; A61Q 3/00; A61Q 1/02; A61Q 1/06; C08K 5/156; C09D 7/1233; A01N 25/00
See application file for complete search history.

(56) References Cited

U.S. PATENT DOCUMENTS

| | | |
|---|---|---|
| 1,934,309 A | 11/1933 | Hoover |
| 2,004,115 A | 6/1935 | Izard |

(Continued)

FOREIGN PATENT DOCUMENTS

| | | |
|---|---|---|
| CA | 1000285 | 11/1976 |
| CA | 2347255 A1 | 2/2004 |

(Continued)

OTHER PUBLICATIONS

Arthur K. Doolittle, Application of a Mechanistic Theory of Solvent Action to Plasticizers and Plasticization, 2 J Pol. Sci. 121 (1947).*

(Continued)

*Primary Examiner* — Sean Basquill
(74) *Attorney, Agent, or Firm* — Cantor Colburn LLP

(57) ABSTRACT

Disclosed herein is a dispersion comprising a liquid or semi-solid continuous phase, a dispersed solid phase comprising a plurality of organic, inorganic or inorganic-organic particles, and an alkyl ketal ester having the structure

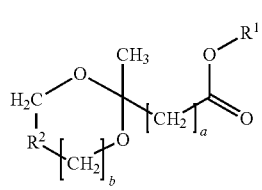

wherein a is 0 or an integer of 1 to 12, specifically 1 to 6, more specifically 1 to 4; b is 0 or 1; $R^2$ is a divalent $C_{1-8}$ group optionally substituted with up to 5 hydroxyl groups; and $R^1$ is $C_{1-6}$ alkyl, and wherein at least a portion of the alkyl ketal ester is present in the continuous phase, on a surface of at least some of the dispersed particles, or a combination thereof.

25 Claims, No Drawings

(51) Int. Cl.
*A61Q 9/04* (2006.01)
*A61Q 15/00* (2006.01)
*A61Q 17/04* (2006.01)
*C08K 5/156* (2006.01)

(56) References Cited

U.S. PATENT DOCUMENTS

| | | | |
|---|---|---|---|
| 2,008,720 A | | 7/1935 | Lawson |
| 2,260,261 A | | 10/1941 | Morey et al. |
| 2,556,135 A | | 6/1951 | Croxall et al. |
| 2,654,723 A | | 10/1953 | Greene |
| 2,985,536 A | | 5/1961 | Stein et al. |
| 3,201,420 A | | 8/1965 | Fuzesi et al. |
| 3,658,789 A | | 4/1972 | Fried |
| 3,855,248 A | | 12/1974 | Lannert et al. |
| 4,153,064 A | | 5/1979 | Sawada et al. |
| 4,460,767 A | | 7/1984 | Matsumura et al. |
| 4,737,426 A | | 4/1988 | Roth |
| 4,792,411 A | | 12/1988 | Walsh |
| 4,806,448 A | | 2/1989 | Roth |
| 4,897,497 A | | 1/1990 | Fitzpatrick |
| 5,013,543 A | * | 5/1991 | Mercado et al. ............... 424/63 |
| 5,093,111 A | * | 3/1992 | Baker et al. .................... 424/64 |
| 5,266,592 A | | 11/1993 | Grub et al. |
| 5,419,848 A | | 5/1995 | Van Eenam |
| 5,516,459 A | | 5/1996 | Van Eenam |
| 5,608,105 A | | 3/1997 | Fitzpatrick |
| 5,700,522 A | | 12/1997 | Nonweiler et al. |
| 5,705,087 A | | 1/1998 | Mushrush et al. |
| 5,859,263 A | | 1/1999 | Ghorpade et al. |
| 5,917,059 A | | 6/1999 | Bruchmann et al. |
| 5,998,092 A | | 12/1999 | McCulloch et al. |
| 6,010,995 A | | 1/2000 | Van Eenam |
| 6,083,490 A | | 7/2000 | Ellis et al. |
| 6,130,195 A | | 10/2000 | Doyel et al. |
| 6,306,249 B1 | | 10/2001 | Galante et al. |
| 6,395,810 B1 | | 5/2002 | Luitjes et al. |
| 6,423,480 B2 | | 7/2002 | Ichiki |
| 6,423,677 B1 | | 7/2002 | Van Eenam |
| 6,451,223 B1 | | 9/2002 | Jeon |
| 6,627,181 B1 | * | 9/2003 | Busch et al. .................... 424/61 |
| 6,749,998 B2 | | 6/2004 | Schwartzkopf et al. |
| 6,806,392 B2 | | 10/2004 | Boesch et al. |
| 6,844,302 B1 | | 1/2005 | Boden et al. |
| 7,094,395 B1 | * | 8/2006 | Qu et al. ......................... 424/63 |
| 7,153,996 B2 | | 12/2006 | Fagan et al. |
| 7,503,970 B2 | | 3/2009 | Dransfield et al. |
| 7,705,081 B2 | | 4/2010 | Porzio et al. |
| 2003/0167681 A1 | | 9/2003 | Delgado Puche |
| 2004/0138090 A1 | | 7/2004 | Drapier et al. |
| 2004/0147602 A1 | | 7/2004 | Smith et al. |
| 2004/0157759 A1 | | 8/2004 | Scherubel |
| 2004/0167245 A1 | | 8/2004 | Chappelow et al. |
| 2005/0233927 A1 | | 10/2005 | Scherubel |
| 2006/0165622 A1 | | 7/2006 | Hiramoto |
| 2006/0207037 A1 | | 9/2006 | Fadel et al. |
| 2007/0111917 A1 | | 5/2007 | Lang et al. |
| 2007/0161530 A1 | | 7/2007 | Kaneda et al. |
| 2008/0096785 A1 | | 4/2008 | Egbe et al. |
| 2008/0124426 A1 | | 5/2008 | Kobler et al. |
| 2008/0188603 A1 | | 8/2008 | Porzio et al. |
| 2008/0242721 A1 | | 10/2008 | Selifonov |
| 2008/0305978 A1 | | 12/2008 | Wietfeldt et al. |
| 2009/0281012 A1 | | 11/2009 | Trivedi et al. |
| 2010/0087357 A1 | | 4/2010 | Morgan, III et al. |
| 2011/0196081 A1 | | 8/2011 | Kwon et al. |
| 2011/0300083 A1 | * | 12/2011 | Yontz et al. .................... 424/59 |

FOREIGN PATENT DOCUMENTS

| | | |
|---|---|---|
| DE | 10036423 A1 | 3/2001 |
| EP | 012543 A1 | 6/1980 |
| EP | 0308956 A2 | 3/1989 |
| EP | 0507190 A1 | 3/1992 |
| EP | 0913463 A1 | 5/1999 |
| JP | 284327 A | 9/1953 |
| JP | 2800437 A | 9/1953 |
| JP | 2006143702 A | 6/2006 |
| SU | 722912 | 3/1980 |
| WO | 9412489 A1 | 6/1994 |
| WO | 2005095378 A2 | 10/2005 |
| WO | 2006089873 A1 | 8/2006 |
| WO | 2007/062118 A2 | 5/2007 |
| WO | WO 2007/062118 * | 5/2007 ........... C07D 407/02 |
| WO | WO2007062158 A2 | 5/2007 |
| WO | 2007094922 A2 | 8/2007 |
| WO | 2008089463 A2 | 7/2008 |
| WO | 2009/032905 A1 | 3/2009 |
| WO | WO2009032905 A1 | 3/2009 |
| WO | 2009/048874 A1 | 4/2009 |
| WO | 2010151558 A1 | 12/2010 |

OTHER PUBLICATIONS

Written Opinion for PCT/US2011/035974 mailed Jan. 12, 2012, 5 pages.

Bechtold, et al., "Perfectly Alternating Copolymer of Lactic Acid and Ethylene Oxide as a Plasticizing Agent for Polylactide," Macromolecules 34: 8641-8648 (2001).

Bozell, et al., "Production of levulinic acid and use as a platform chemical for derived products," Resources, Conservation and Recycling 28: 227-239 (2000).

Corma, et al., "Chemical Routes for the Transformation of Biomass into Chemicals," Chem. Rev. 107: 2411-2502 (2007).

Cuiling, et al., "Synthesis of Levulinic Ketals with Furfuryl Alcohol as Raw Material," Journal of Huaqiao University (Nature Science) 23(3): 257-259 (2002) (English Translation).

Girisuta, Buana "Levulinic Acid from Lignocellulosic Biomass," Rijksuniversiteit Groningen, pp. 1-149, Nov. 2007.

Gonzalez, et al., "Application of Fourier Transform Infrared Spectroscopy in the Study of Interactions Between PVC and Plasticizers: PVC/Plasticizer Compatibility versus Chemical Structure of Plasticizer," Journal of Applied Polymer Science 101: 1731-1737 (2006).

Haskelbhrg, L., "The preparation of glycerol esters of amino acids," Compt. rend. 190270-190272 (1930).

Hoydonckx, et al., "Esterification and transesterification of renewable chemicals," Topics in Catalysis 27(1-4): 83-96 (2004).

http://www.thegoodscentscompany.com/data/rw1597311.html.

Krauskopf, Leonard G., "How About Alternatives to Phthalate Plasticizers?," Journal of Vinyl & Additive Technology 9(4): 159-171 (2003).

Ma, et al., "Biodiesel production: a review," Bioresource Technology 70: 1-15 (1999).

Meher, et al., "Technical aspects of biodiesel production by transesterification—a review," RSER 194: 1-21 (2004).

Meltzer, et al., "2,2-Disubstituted 1,3-Dioxolanes and 2,2-Disubstituted 1,3-Dioxanes," JOC 25: 712-715 (1960).

Meskens, Frans A.J., "Methods for the Preparation of Acetals from Alcohols or Oxiranes and Carbonyl Compounds," Synthesis 501-522 (1981).

Miller, et al., "Biorenewable Fuels and Chemicals via Reactive Distillation," Midtech Midland, May 11, 2006 ( Powerpoint Presentation).

Moncrieff, R.W., "Ketals," The Journal of the American Oil Chemist's Society 259-261 (1947).

Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001).

Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).

Showler, et al., "Condensation Products of Glycerol with Aldehydes and Ketones. 2-Substituted m-Dioxan-5-OLS and 1,3-dioxolane-4-methanols," Chem. Rev. 67: 427-440 (1967).

(56) References Cited

OTHER PUBLICATIONS

Takenishi, et al., The Syntheses from Levulinic Acid. A Possible Use of Some 2 Methyl-5-oxopyrrolidine-2 carboxylic Esters as Plasticizers, 27(4): 207-209 (1954).
Timokhin, et al., "Levulinic acid in organic synthesis," Russian Chemical Reviews 68(1) 73-84 (1999).
Wardzinska, et al., "Influence of the Glycol Component in Dibenzoate Plasticizers on the Properties of Plasticized PVC Films," Journal of Applied Polymer Science 97: 822-824 (2005).
Werpy, et al., "Top Value Added Chemicals from Biomass—vol. I—Results of Screening for Potential Candidates from Sugars and Synthesis Gas," Biomass 1-69 (2004).
Wood, et al., "Cyclic polyesters: 1. Preparation by a new synthetic method, using polymer-supported reagants," Polymer 34(14): 3052-3058 (1993).
Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Yulan, et al., "Synthesis of Ketals of 4-Oxopentanoates," Lanzhou Daxue Xuebao, Ziran Kexueban 30(2): 66-70 (1994).
Zhang, et al., "Synthesis of Ketals of 4-Oxopentanoates," Lanzhou Daxue Xuebao, Ziran Kexueban 30(2): 66-70 (1994).
International Preliminary Report on Patentability for International Application No. PCT/US2011/035974, mailed Nov. 13, 2012, 7 pages.
International Search Report for PCT/US2011/035974, mailed Jan. 12, 2012, 6 pages.
Black, Cline, et al., "The Solubility of Water in Hydrocarbons", The Journal of Chemical Physics, vol. 16, pp. 537-543 (1948).
"Pigment", http://en.wikipedia.org/wiki/Pigment, English version downloaded from the Internet on Jan. 7, 2015, 6 pages.
Extended European Search Report for European Application No. 11781171.1; Search Report Date Dec. 19, 2014; 10 pages.
Brigl, et al., "The Reaction of the Pyruvic Acid with Glycerin," Annalen der Chemie 476: 215-232 (Received Oct. 7, 1929) (with English translation).
Hexyl Cellosolve(R) Solvent, DOW Technical Data Sheet, 3 pages (2012).
Holmberg, Krister, "Surfactants with controlled half-lives", Current Opinion in Colloid & Interface Science, vol. 1, Issue 5, pp. 572-579 (Oct. 1996).
Eastman Chemical Company. (May 2006). Selecting Coupling Agents for Multi-phase Models. Retrieved Aug. 13, 2009, from http://www.eastman.com/Literature Center/M/M207.pdf.
Horsfall, et al., "Fungitoxicity of Dioxanes, Dioxolanes, and Methylenedioxybenzenes," The Connecticut Agricultrual Experiment Station New Haven, Bulletin 673: 1-44, Jun. 1965.

* cited by examiner

ALKYL KETAL ESTERS AS DISPERSANTS AND SLIP AGENTS FOR PARTICULATE SOLIDS, METHODS OF MANUFACTURE, AND USES THEREOF

CROSS-REFERENCE TO RELATED APPLICATIONS

This application claims the benefit of U.S. Provisional Application No. 61/332,978, filed May 10, 2010, which is incorporated herein by reference in its entirety, and to U.S. Provisional Application No. 61/332,982, which is incorporated herein by reference in its entirety.

FIELD OF INVENTION

This invention relates to dispersions of solid particles in a continuous phase, methods of their manufacture, and their uses.

BACKGROUND

A large number of products include particulate solids dispersed in a liquid, solid, or semi-solid continuous phase. Pigments are a very common example of solids that are dispersed in such a manner. Pigments are widely used in paints, inks, toners, colored pencil leads, cosmetics, and a number of other applications.

A large number of additives can be used to aid dispersion of the solid particles in the continuous phase, for example certain cosolvents, surfactants slip additives, block copolymer dispersants, and thickeners. These are generally selected for their affinity to the particle surface, which allows them to at least partially attach to the particle surface and in that way render the surface more compatible with the dispersing medium. Some, in particular slip agents, also tend to lubricate the particles so that they do not stick to each other. Thickeners, which reside mainly or exclusively in the continuous phase, increase the viscosity of the continuous phase so there is a kinematic barrier to particle settling. Determination of the most appropriate dispersant, slip additives, or thickener for a given formulation therefore, can be time-consuming. Further, despite the large number of dispersants slip additives, and thickeners available, there remains a need in the art for materials that can be used in a wide variety of different systems, including liquid and semi-solid systems.

SUMMARY

Disclosed herein is a dispersion comprising a liquid or semi-solid continuous phase, a dispersed solid phase comprising a plurality of organic, inorganic or inorganic-organic particles, and an alkyl ketal ester having the structure

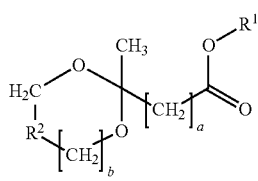

I wherein a is 0 or an integer of 1 to 12, specifically 1 to 6, more specifically 1 to 4; b is 0 or 1; $R^2$ is a divalent $C_{1-8}$ group optionally substituted with up to 5 hydroxyl groups; and $R^1$ is $C_{1-6}$ alkyl, and wherein at least a portion of the alkyl ketal ester is present in the continuous phase, on a surface of at least some of the dispersed particles, or a combination thereof.

A method of forming the foregoing dispersion comprises combining the continuous phase, plurality of solid particles, and alkyl ketal ester to form the dispersion.

Further disclosed are coating compositions and cosmetics comprising the foregoing dispersions.

A particulate solid, comprises a plurality of solid particles; and an alkyl ketal ester at least partially coating at least some of the particles, the alkyl ketal ester having the structure:

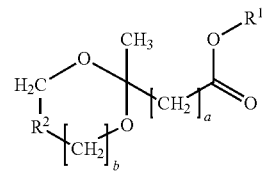

I wherein a is 0 or an integer of 1 to 12, specifically 1 to 6, more specifically 1 to 4; b is 0 or 1; $R^2$ is a divalent $C_{1-8}$ group optionally substituted with up to 5 hydroxyl groups; and $R^1$ is $C_{1-6}$ alkyl.

Further disclosed are coating compositions and cosmetics comprising the foregoing particulate solids.

The invention is further illustrated by the following Detailed Description, Examples, and Claims.

DETAILED DESCRIPTION

Applicants have found that alkyl ketal esters having the general formula I are excellent dispersants and slip agents for a variety of organic, inorganic and inorganic-organic particles. As such, the alkyl ketal esters are useful additives in a variety of dispersions of particles into a variety of liquid and semi-solid dispersing media (continuous phases). Examples of these dispersions are paints and other coatings, inks, toners, pencil leads, and various types of cosmetic products, as well as many others. The alkyl ketal esters are also useful in solid formulations containing the organic, inorganic, and inorganic-organic particles. In a particularly advantageous feature, the alkyl ketal esters can be bio-based, that is derived at least in part from a natural source.

The alkyl ketal esters useful herein include those having the general structure I

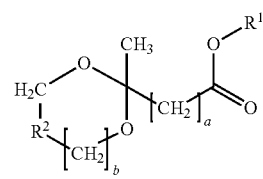

I wherein
a is 0 or an integer of 1 to 12, specifically 1 to 6, more specifically 1 to 4;
b is 0 or 1;
$R^2$ is a divalent $C_{1-8}$ group optionally substituted with up to 5 hydroxyl groups, specifically methylene, ethylidene (>CH—CH$_3$), >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH; and $R^1$ is C$_{1-6}$ alkyl, specifically a C$_{1-4}$ alkyl, more specifically a C$_{1-2}$ alkyl.

Some compounds within the scope of Structure I contain one or more chiral carbon atoms; structure I does not distinguish among those possible stereoisomers and is intended to include all such stereoisomers. In a specific embodiment, a is 1 to 4, b is 0 or 1, and $R^2$ is >CH—CH$_3$, >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH. In a specific embodiment, a is 1 to 4, b is 0 or 1, and $R^2$ is >CH—CH$_3$, >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH.

When b is 0, the alkyl ketal ester includes a five-membered ring; when b is 1, it includes a six-member ring. In a specific embodiment, b is 0.

In some embodiments, b is 0 and $R^2$ is one of methylene, ethylidene or >CH—CH$_2$OH. In other embodiments, b is 1 and $R^2$ is methylene.

In one embodiment, $R^1$ contains 1 or 2 carbon atoms.

Specific alkyl ketal esters include those corresponding to the reaction formulations of 1,2-ethylene glycol with the methyl, ethyl, n-propyl or n-butyl ester of levulinic acid; of 1,2-propylene glycol with the methyl, ethyl, n-propyl or n-butyl ester of levulinic acid; of 1,3-propane diol with the methyl, ethyl, n-propyl or n-butyl ester of levulinic acid; of glycerine with the methyl, ethyl, n-propyl, or n-butyl ester of levulinic acid; of trimethylolethane with the methyl, ethyl, n-propyl, or n-butyl ester of levulinic acid; of trimethylolpropane with the methyl, ethyl, n-propyl, or n-butyl ester of levulinic acid; of pentaerythritol with the methyl, ethyl, n-propyl, or n-butyl ester of levulinic acid; of erythritol with the methyl, ethyl, n-propyl, or n-butyl ester of levulinic acid; of sorbitol with the methyl, ethyl, n-propyl, or n-butyl ester of levulinic acid; of 1,2-ethylene glycol with methyl, ethyl, n-propyl, or n-butyl acetoacetate; of 1,2-propylene glycol with methyl, ethyl, n-propyl, or n-butyl acetoacetate; of 1,3-propane diol with methyl, ethyl, n-propyl, or n-butyl acetoacetate; of glycerine with methyl, ethyl, n-propyl, or n-butyl acetoacetate; of trimethylolethane with methyl, ethyl, n-propyl or n-butyl acetoacetate; of trimethylolpropane with methyl, ethyl, n-propyl, or n-butyl acetoacetate, or erythritol with methyl, ethyl, n-propyl, or n-butyl acetoacetate; of pentaerythritol with methyl, ethyl, n-propyl, or n-butyl acetoacetate; or of sorbitol with methyl, ethyl, n-propyl, or n-butyl acetoacetate.

Specific alkyl ketal esters include those having the following structures II-VI. An embodiment includes alkyl ketal esters of structure II

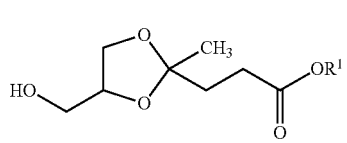

(II)

wherein $R^1$ is methyl, ethyl, n-propyl, or n-butyl. When $R^1$ is methyl, this structure is referred to herein as "methyl-LGK," and corresponds to the reaction formulation of methyl levulinate with glycerine. Methyl-LGK is miscible with water in all proportions.

When $R^1$ in structure II is ethyl, this structure is referred to herein as "ethyl-LGK," or "Et-LGK" and corresponds to the reaction formulation of ethyl levulinate with glycerine. Ethyl-LGK is miscible in water in all proportions. Ethyl-LGK also dissolves or is miscible with a large number of hydrophobic and hydrophilic organic compounds to the extent of at least 20 parts of the organic compound in 80 parts of ethyl-LGK. Examples of such organic compounds include methanol, ethanol, tetrahydrofuran, acetone, ethyl acetate, ethyl laurate, lauric acid, methylene chloride, toluene, acetic acid, low molecular weight poly(propylene glycol), and castor oil.

When $R^1$ in structure II is n-propyl, this structure is referred to herein as "n-propyl-LGK," and corresponds to the reaction formulation of n-propyl levulinate with glycerine. n-Propyl-LGK is miscible with water to the extent of about 1 part per 99 parts water.

When $R^1$ in structure II is n-butyl, this structure is referred to herein as "n-butyl-LGK" or "Bu-LGK," and represents the reaction formulation of n-butyl levulinate with glycerine. n-Butyl-LGK is miscible in water to the extent of about 1 part per 99 parts of water. It dissolves or is miscible with various organic compounds to the extent of at least 20 parts of the organic compound in 80 parts of N-butyl-LGK. Examples of such organic compounds include alcohols (including ethanol and 1,2-butylene glycol), organic esters (such as C$_{12-14}$ alkyl benzoates, isopropyl myristate and octyl palmitate), and many vegetable oils (including castor, corn, soy and safflower oils).

Another embodiment includes alkyl ketal esters of structure III

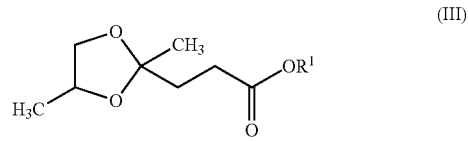

(III)

wherein $R^1$ is methyl, ethyl, n-propyl, or n-butyl. When $R^1$ is methyl, the structure is referred to herein as "methyl-LPK" and corresponds to the reaction formulation of methyl levulinate with 1,2-propylene glycol.

When $R^1$ in structure III is ethyl, this structure is referred to herein as "ethyl-LPK" or "Et-LPK," and corresponds to the reaction formulation of ethyl levulinate with 1,2-propylene glycol. Ethyl-LPK is miscible in water to the extent of 2.5 parts in 97.5 parts of water. Ethyl-LPK dissolves or is miscible with a variety of organic compounds of varying hydrophilicity, to the extent of at least 20 parts of the organic compound in 80 parts of ethyl-LPK. These organic compounds include, for example, methanol, ethanol, tetrahydrofuran, acetone, ethyl acetate, methylene chloride, toluene, cyclohexane, acetic acid, low molecular weight poly(propylene glycol), mineral oil, castor oil, canola oil, corn oil, and sunflower oil.

When $R^1$ in structure III is n-butyl, this structure is referred to herein as "n-butyl-LPK" or "Bu-LPK," and represents the reaction formulation of n-butyl levulinate with 1,2-ethylene glycol. n-butyl-LPK dissolves or is miscible with various organic compounds to the extent of at least 20 parts of the organic compound in 80 parts of N-butyl-LPK. Examples of such organic compounds include alcohols (including ethanol and 1,2-butylene glycol), organic esters (such as $C_{12-14}$ alkyl benzoates, isopropyl myristate and octyl palmitate), and many vegetable oils (including castor, corn, soy and safflower oils).

Another embodiment includes alkyl ketal esters of structure IV

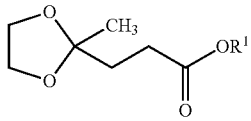

(IV)

wherein $R^1$ is methyl, ethyl, n-propyl, or n-butyl. When $R^1$ is ethyl, this structure is referred to herein as "ethyl-LEK," and corresponds to the reaction formulation of ethyl levulinate with 1,2-ethylene glycol. Ethyl-LEK is miscible in water to the extent of 5 parts per 95 parts of water.

Another embodiment includes alkyl ketal esters of structure V

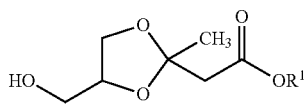

(V)

wherein $R^1$ is methyl, ethyl, n-propyl, or n-butyl. When $R^1$ is methyl, this structure is referred to herein as "Me-AcAcGK," and represents the reaction formulation of methyl acetoacetate with glycerine. When $R^1$ is ethyl, this structure is referred to herein as "Et-AcAcGK," and represents the reaction formulation of ethyl acetoacetate with glycerine. Me-AcAcGK and Et-AcAcGK each are miscible with water in all proportions.

Another embodiment includes alkyl ketal esters of structure VI

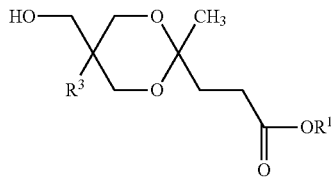

wherein $R^1$ is methyl, ethyl, n-propyl, or n-butyl and $R^3$ is methyl or ethyl. Compounds according to structure VI correspond to the reaction formulation of trimethylolethane ($R^3$ is methyl) or trimethylolpropane ($R^3$ is ethyl) and a $C_{1-4}$ ester of levulinic acid. When $R^1$ is ethyl, and $R^3$ is methyl, this structure is referred to herein as "ethyl-LTMEK," and when $R^1$ is ethyl, and $R^3$ is ethyl, this structure is referred to herein as "ethyl-LTMPK."

The alkyl ketal esters of structures I-VI can be prepared by reacting an alkyl keto ester of structure VII

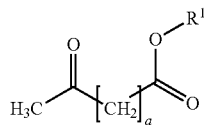

(VII)

with the appropriate polyol of structure VIII

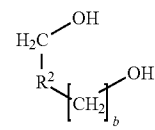

I wherein a, b, $R^2$ and $R^1$ are as defined in structure I. Specific ketoesters include $C_1$-$C_4$ alkyl esters of pyruvic acid, acetoacetic acid, levulinic acid, α-ketobutyric acid, α-ketoisovaleric acid, 5-ketohexanoic acid, α-ketoisocaproic acid, 4-acetylbutyric acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, and 2-oxo-3-butynoate. Specific polyols include ethylene glycol, 1,2-propylene glycol, 1,3-propane diol, glycerine, trimethylolethane, trimethylolpropane, erythritol, pentaerythritol, or sorbitol. This reaction can be performed in the presence of an acid catalyst. A preferred process is described in WO 09/032905.

In preferred embodiments, the keto ester is a $C_1$-$C_4$ alkyl ester of levulinic acid (4-oxopentanoic acid). Levulinic acid is an abundant feedstock that is prepared on an industrial scale by acidic degradation of hexoses and hexose-containing polysaccharides such as cellulose, starch, sucrose, and the like. Other preferred keto esters include $C_1$-$C_4$ alkyl esters of pyruvic acid and acetoacetic acid. Especially preferred keto esters include ethyl levulinate, n-propyl levulinate, and n-butyl levulinate.

The term "miscible" and its variations ("miscibility", "compatibility", and the like) are used herein as a synonym for "soluble", i.e., a mixture of the materials by themselves form a "true" solution, in which one material is molecularly dispersed in the other, or in which one material is dispersed as droplets which have a longest dimension of less than 200 nm, such that the mixture is optically clear. In an exemplary embodiment, the longest dimension is a "radius of gyration." As used herein, a material that is "miscible" or "fully miscible" in another, without further qualification, is miscible with that other material in all proportions, i.e., in mixtures that contain the two components by themselves in all weight ratios from 99:1 to 1:99. A fully miscible alkyl ketal ester is soluble in another material, such as water, at all proportions from 99:1 to 1:99. A partially miscible alkyl ketal ester is immiscible in another material in proportions from greater than 30 parts of the alkyl ketal ester in 70 parts or less of the other material and miscible in other combinations. A sparingly miscible alkyl ketal ester is immiscible in another material or miscible in another material to the extent of less than 10 parts in 90 parts of the other material. A material is "immiscible" in another if it is not soluble by itself in that material to the extent of at least 1 part per 99 parts of the other. Unless stated otherwise, miscibility is assessed at 25° C. The foregoing alkyl ketal esters can be classified as fully water-miscible, partially water-miscible, or sparingly water-miscible. By "macroscopically uniform," it is meant that the formulation is uniform when viewed at a length scale of at least 10 micrometers.

The selection of a particular alkyl ketal ester for a particular formulation will depend at least in part upon the function or functions that the alkyl ketal ester is expected to perform in the formulation, as well as the other ingredients of the formulation. For example, when the alkyl ketal ester is present to disperse hydrophobic particles into an aqueous continuous phase, a partially- or fully-water miscible alkyl ketal ester is selected. If the particles are highly hydrophobic, a mixture of a partially- or fully-water miscible alkyl ketal ester with a sparingly water-miscible alkyl ketal ester can be used. In a coating formulation, the specific alkyl ketal ester may be chosen to have a particular volatility profile so that the coating dries at a desired rate, or because of its ability to carry out additional functions (e.g., coalesced latex particles). Similarly, in cosmetic formulations, the specific alkyl ketal ester may be chosen for its feel on the skin (i.e., emolliency)

When the alkyl ketal ester is present to disperse particles into an alcoholic phase or an alcohol/water mixture, the alkyl ketal ester is preferably miscible in the alcohol, for example to the extent of 10 parts in 90 parts of the alcohol, and can be fully miscible in the alcohol. Alkyl ketal esters that are fully or partially miscible in the alcohol can be present in a mixture with one or more alkyl ketal esters that are only sparingly soluble in the alcohol. This can allow, for example, the alcohol/miscible alkyl ketal ester mixture to function as a cosolvent mixture in which the sparingly soluble alkyl ketal ester is dissolved. The sparingly soluble alkyl ketal ester can in turn compatibilize another material into the formulation. In some alcoholic systems and alcohol/water systems, the alkyl ketal ester performs a compatibilization and/or emulsification function, such as to compatibilize or emulsify aqueous and oil phases in an emulsion. The alcohol in such an alcoholic phase or alcohol/water mixture is a lower alcohol, including $C_{1-7}$ alkanols such as ethanol, 1-propanol, 2-propanol, 1-butanol, 2-butanol, t-butanol, 1-pentanol, 1-hexanol, as well as the various other isomers of pentanol and hexanol; alkylene glycols such as ethylene glycol, diethylene glycol, triethylene glycol, 1,2-propylene glycol, 1,3-propane diol, dipropylene glycol, tripropylene glycol 1,4-butane diol and 1,2-butane diol; triols such as glycerine, and the like, and is preferably ethanol, 1,2-propylene glycol, glycerol, or 1,3-propane diol.

When the alkyl ketal ester is present to disperse particles into an oil phase, the alkyl ketal ester can be a partially-water miscible type or a sparingly water-miscible type. It is also possible in some cases to use fully-water-miscible types in that instance.

A wide variety of particles can be used in the particulate solid phase. The particles are a crystalline or non-crystalline solid under the conditions of manufacture, storage, and use, and can be organic, inorganic, or inorganic-organic. "Inorganic-organic" as used herein means a material that has both inorganic and organic components, such as an organic material that is precipitated by interaction with an inorganic material precipitated onto an inorganic particle (as a lake pigment), or otherwise sorbed onto and/or into the particle. In some cases, the particles can be surface treated through reaction with the functional groups on the surface, e.g., by silanation, zirconation, or addition of a cyclic dimethylsiloxane. Surface treatments can change the wetting or dispersing characteristics or be used for aesthetic effect. The particles are insoluble in the alkyl ketal ester (although it can absorb the alkyl ketal ester or in some cases be swelled by the alky ketal ester), and are insoluble in any other dispersant or the continuous phase in which they are contained. The particles can be malleable. The particles can be pigment particles, or other solids including for example natural finely divided ores, minerals, sparingly soluble or insoluble salts, particles of wax or plastic, dyes that are insoluble in the alkyl ketal ester or continuous phase, crop protection and pest control agents, UV absorbers, optical brighteners and polymerization stabilizers.

Organic particles include biological and organic pigments such as quinacridone, alizarin crimson, gamboge, cochineal red, rose madder, Indian yellow, phthalo green, phthalo blue, pigment red 170 and the like.

Inorganic pigments are useful as the solid particulate phase. The pigments can be white, black, or otherwise colored. Mixtures of pigments can be used. Suitable inorganic pigments include, for example, cadmium yellow, cadmium red, cadmium green, cadmium orange, carbon black, ivory black, iron oxide black, chrome yellow, chrome green, cobalt violet, cobalt blue, cerulean blue, aureolin (cobalt yellow), Han purple, Egyptian blue, Paris green, verdigris, viridian, sanguine, caput mortuum, iron oxide red, red ochre, Venetian red, Prussian blue, yellow ochre, raw sienna, burnt sienna, raw umber, burnt umber, lead white, cremnitz white, Naples yellow, red lead, vermilion, titanium yellow, titanium beige, titanium oxide, titanium black, ultramarine, ultramarine green and the like.

Inorganic-organic pigments include the so-called "Lake" pigments such as the various Red Al Lake, Red Ba Lake, Red Zn Lake, Red Talc Lake, Blue Al Lake, Yellow Al Lake pigments, as well as other lake pigments.

Various other inorganic compounds, minerals, and clays are also of interest as the solid particulate phase. These include, for example, calcium carbonate, magnesium aluminum silicate, magnesium trisilicate, attapulgite, bentonite, hectorite, lithium magnesium silicate, lithium magnesium sodium silicate, montmorillonite, boron nitride, silicon nitride, titanium carbide, boron carbide, mullite, coreiderite, and the like.

Metal powders are also useful as the solid particulate phase. Examples of these include aluminum, iron, steel, silver, bronze, copper, chromium, and the like.

The particles can have a particle size as small as about 10 nanometers up to 100 micrometers, for example from 10 nanometers to 25 micrometers. A more typical particle size is from 100 nanometers to 25 micrometers.

In an embodiment, a dispersion comprises a liquid or semi-solid continuous phase, at least one organic, inorganic, or inorganic-organic particulate dispersed within the continuous phase, an alkyl ketal ester I present in the continuous phase and/or on the surface of the dispersed particles. Metallic pigments can be highly elongated in shape and may be as large as several hundred micrometers in length.

A wide variety of materials and formulations can be used as the liquid or semi-solid phase. Liquid phases are flowable, and can be aqueous, organic, or a combination thereof, for example a combination of water and a water-miscible alcohol or other organic solvent. Semi-solid phases can be thixotropic, that is, flowable under a force. Semi-solids include gels, malleable materials such as waxes, wax blends, or wax/oil blends, amorphous and semi-crystalline polymers, and combinations thereof. It is to be understood that the term "continuous phase" is used in contrast to the solid particulate phase. Thus, a continuous phase can itself have more than one phase, for example an oil-in-water or a water-in-oil emulsion, a latex, or a semi-crystalline polymer. When the continuous phase is an emulsion, the solid particles will generally be present in the continuous phase of the emulsion, although it is possible for the particles to be sequestered in the discontinuous phase of the emulsion.

Other adjuvants can be present in the dispersions (for example the ink dispersions described below), depending on the intended use of the dispersion. These other adjuvants include, for example, other wetting agents that enhance the particle wetting; and other dispersants and surfactants that further enhance dispersion and or dispersion stability; and combinations comprising at least of the foregoing. Anionic, cationic, amphoteric, or nonionic surface-active compounds are typically used for these purposes, for example compounds having one or more $C_8$ or longer hydrocarbyl chains, in some instances also having aromatic ring groups. Specific, nonlimiting examples are alkyl sulfates such as lauryl sulfate, stearyl sulfate, or octadecyl sulfate, primary alkyl sulfonates such as dodecyl sulfonate, and secondary alkyl sulfonates, particularly the $C_{13}$-$C_{17}$ alkanesulfonate sodium salt, alkyl phosphates, alkylbenzenesulfonates such as dodecylbenzenesulfonic acid, and salts thereof. Also useful are soy lecithin and condensation products of fatty acid and turbine or hydroxyethanesulfonic acid, similarly alkoxylation products of alkylphenols, castor oil resin esters, fatty alcohols, fatty amines, fatty acids and fatty acid amides, which alkoxylation products can similarly have ionic end groups, for example in the form of sulfosuccinic monoesters or else as sulfonic, sulfuric and phosphoric esters, and also salts thereof (sulfonates, sulfates or phosphates). Alkoxylated addition compounds obtained by reaction of polyepoxides with amines or bisphenol-A or bisphenol-A derivatives with amines can also be used. Nonionic alkoxylated styrene phenol condensates can be used, for example those obtained by addition of optionally substituted styrenes onto optionally substituted phenols and reaction with ethylene oxide and/or propylene oxide, as well as ionically modified derivatives thereof, for example as sulfonic, sulfuric and phosphoric esters, and salts thereof (sulfonates, sulfates or phosphates). Other useful surface-active compounds include lignosulfonates and polycondensates of naphthalinesulfonic acid and formaldehyde, or else of alkylarylsulfonic acids, haloarylsulfonic acid, sulfonated phenols, or sulfonated naphthols with formaldehyde.

Another class of adjuvants includes organic solvents or water-soluble hydrotropic substances. Hydrotropic substances can also serve as a solvent, and can be monomeric, oligomeric, or polymeric, for example formamide, urea, tetra-methylurea, ε-caprolactam, ethylene glycol, propylene glycol, diethylene glycol, triethylene glycol, polyethylene glycol, α-methyl ω-hydroxy polyethylene glycol ether, dimethyl polyethylene glycol ether, dipropylene glycol, polypropylene glycol, dimethyl polypropylene glycol ether, copolymers of ethylene glycol and propylene glycol, butyl glycol, methylcellulose, glycerol, diglycerol, polyglycerol, N-methyl-pyrrolidone, 1,3-diethyl-2-imidazolidinone, thiodiglycol, sodium benzenesulfonate, sodium xylenesulfonate, sodium toluenesulfonate, sodium cumenesulfonate, sodium dodecylsulfonate, sodium benzoate, sodium salicylate, sodium butyl monoglycol sulfate, cellulose derivatives, gelatin derivatives, polyvinylpyrrolidone, polyvinyl alcohol, polyvinylimidazole and co- and terpolymers of vinylpyrrolidone, vinyl acetate and vinylimidazole. Polymers comprising vinyl acetate building blocks may subsequently be saponified to the vinyl alcohol.

Also useful in the dispersions are, for example thickeners, preservatives, viscosity stabilizers, grinding assistants, fillers, antisettling agents, photoprotectants, antioxidants, degassers/defilmers, foam-reducing agents, anticaking agents, and viscosity and rheology improvers. Useful viscosity regulators include polyvinyl alcohol, and cellulose derivatives, including polysaccharides, associative thickeners, such as hydrophobically modified nonionic systems (such as hydrophobe modified ethoxylate urethane), hydrophobically modified cellulosics (such as hydrophobe modified hydroxyethyl cellulose), and hydrophobe modified alkali-swellable latex, attapulgite clays, bentonite clays, organoclays, synthetic silicas like precipitate silica, fumed silica, organosilica, and synthetic organic systems such as castor oil derivatives, modified acrylic copolymers, polyethylene glycol, polymerized, and the like. Water-soluble or organic solvent-soluble natural or manufactured resins and polymers may similarly be included as filming or binding agents to enhance bonding strength and abrasion resistance. Useful pH regulators include organic bases, for example such as are amines, for example ethanolamine, diethanolamine, triethanolamine, N,N-dimethylethanolamine, diisopropylamine, aminomethylpropanol or dimethylaminomethylpropanol; or inorganic bases such as sodium hydroxide, potassium hydroxide, lithium hydroxide or ammonia; and organic or inorganic acids. The dispersions can further include fats and oils of vegetable and animal origin, for example beef tallow, palm kernel fat, coconut fat, rapeseed oil, sunflower oil, linseed oil, palm oil, soy oil, groundnut oil and whale oil, cotton seed oil, maize oil, poppy seed oil, olive oil, castor oil, colza oil, safflower oil, soybean oil, thistle oil, sunflower oil, herring oil, and sardine oil. Other oils include tall oil, which is obtained from sulfate or Kraft pulping of pine and other softwoods, and tung oil, which is obtained from seeds of certain trees. Common additives also include saturated and unsaturated higher fatty acids, for example palmitic acid, caprylic acid, capric acid, myristic acid, lauryl acid, stearic acid, oleic acid, linoleic acid, linolenic acid, caproic acid, caprylic acid, arachidic acid, behenic acid, palmitoleic acid, gadoleic acid, erucic acid and ricinoleic acid, licanic acid, eleostearic acid, as well as salts thereof.

The particles can be dispersed into the liquid continuous phase in several ways. They can be wetted with the alkyl ketal ester and optionally one or more other adjuvants, for example a wetting agent, and then dispersed into the liquid continuous phase. The alkyl ketal ester can instead (or in addition) be incorporated into the liquid continuous phase before dispersing the particles. Alternatively, the three components can be simultaneously combined. Other components of the compositions can be added at any step in the foregoing methods.

Thus, in an embodiment, a method of forming a dispersion comprises wetting the organic, inorganic or inorganic-inorganic particles with an alkyl ketal ester I and then mixing the wetted particles with a liquid to form a dispersion in which the liquid forms all or part of the continuous phase and the particles form a disperse phase. In another embodiment, a method of forming a dispersion comprises mixing organic, inorganic, or inorganic-inorganic particles into a continuous liquid phase which contains an alkyl ketal ester I. In still another embodiment, a method of forming a dispersion comprises simultaneously combining the organic, inorganic, or inorganic-inorganic particles, the alkyl ketal ester I, and the liquid of the liquid phase.

In a specific embodiment, the solid particles (or materials for comminution into the solid particles) are predispersed, for example with the alkyl ketal esters I and optionally other wetting agent or dispersing aid. The predispersion is subsequently, depending on the size and/or shape of the particles, finely dispersed or finely dissipated, with or without cooling, using a grinding or dispersing assembly, for example stirrers, dissolvers (sawtooth stirrers), rotor-stator mills, ball mills, stirred media mills such as sand and bead mills, high speed mixers, kneaders, roll stands or high performance bead mills. The fine dispersing or grinding of the solid particles and the ketal ester component is carried on to the desired particle size distribution and can take place at 0 to 100° C., 10 to 70° C., or 20 to 60° C., for example. Following the fine-dispersing operation, the particles can be further diluted with a material of the continuous phase. Concentrates can be formed, for later addition to the other ingredients of the dispersion. Alternatively, the particles can be reduced to the desired particle size, and then combined with the alkyl ketal ester I.

In an embodiment, a dispersion, in particular a coating composition comprises a liquid continuous phase and a dispersed phase comprising particles of a solid pigment. The coating composition further contains an alkyl ketal ester I, which can be present in the continuous phase and/or on the surface of the dispersed pigment particles. The pigment particles can be organic, organic-inorganic, or inorganic. In an embodiment, the pigment particles are inorganic.

The coating composition can be, for example, a paint, a sealant, an ink, or other composition containing dispersed pigment particles. Coating compositions of this type generally contain a continuous liquid phase that can be aqueous (including a mixture of water and a water-miscible solvent such as an alcohol), organic, or in the form of an emulsion; a binder resin; and the pigment. Other adjuvants, for example as described above can be present as is known in the art, depending on the intended purpose of the coating composition.

The coating composition can contain from 20 to 90% by weight of the liquid continuous phase; from 5 to 80% by weight of the binder resin; from 0.5 to 45% by weight, or from 0.5 to 35% by weight of one or more organic or inorganic pigments; and from 0.5 to 60% by weight of the alkyl ketal ester I, or from 1 to 25% by weight or from 1 to 10% by weight, each based on the total weight of the liquid coating composition. In another embodiment, the alkyl ketal ester can be present in an amount effective to function as part of the liquid continuous phase. In these embodiments, coating composition can contain from 5 to 90% by weight of the liquid continuous phase; from 5 to 70% by weight of the binder resin; from 0.5 to 25% by weight, or from 0.5 to 15% by weight of the organic or pigment particles; and from 0.5 to 89.5% by weight, from 1 to 25% by weight, or from 1 to 10% by weight of the alkyl ketal ester I, each based on the total weight of the coating composition.

In a specific embodiment, the coating composition is a paint composition. Paint compositions can be aqueous (e.g., a latex), organic, or in the form of an emulsion (e.g., asphalt emulsion coatings for roofs, which can contain bentonite clay in solid particulate form). Further uses are the production of wood preservation systems, varnishes, and the like.

In another embodiment, the coating composition is a liquid ink, for example for felt tip pens, graphics inks ballpoint pens, and ink jet ink. Inks can be aqueous or organic-solvent based, microemulsion inks, UV-curable inks, and inks that operate in a the hot melt process. Further uses are the production of printing colors, for example, flexographic printing inks or intaglio printing inks. In a specific embodiment, the liquid printing inks can be used in any ink-jet printers, particularly those using the bubble jet or piezo process. These liquid printing inks can be used to print paper and also natural or synthetic fiber materials, foils and plastics. Additionally, the coating compositions can be used for printing various kinds of coated or uncoated substrate materials, for example for printing paper board, cardboard, wood, and wood-based materials, metallic materials, semiconductor materials, ceramic materials, glasses, glass and ceramic fibers, inorganic materials of construction, concrete, leather, comestibles, cosmetics, skin and hair. The substrate material may be two-dimensionally planar or spatially extended, i.e., three-dimensionally configured, and may be printed or coated completely or only in parts.

The dispersions comprising a liquid or semi-solid continuous phase, a particulate phase dispersed within the continuous phase, and alkyl ketal ester I can be used as cosmetic formulations and products, for example in wet foundations, skin care products, eyeliner, mascara, or lip care product. For convenience, the liquid or semi-solid continuous phases may be referred to herein as a "carrier." The dispersed particles can be pigments or other types of particles, for example silica, mica, or an active agent such as benzoyl peroxide, or other solids in particulate form. Eye care products are products to be applied on the eye lids, around the eyes, on the eyebrows, or on the eyelashes, and can include eyeshadow, eyeliner, and mascara. Skin products are products applied on the skin (face or body), and can include lotions and creams for hand, face, or body, deodorant/anti-perspirant, and facial cosmetics like foundation, concealer, blush, bronzer, and the like. Lip care products are products applied to the lips, and can include lipstick, lipgloss, lipbalm, lip liner pencil, lip liner pencil stick, and the like. Nail products are products applied to a the nails or cuticles (or both), and can include nail polishes.

Wet foundations are typically liquids or creams. They typically contain an aqueous liquid phase and an oily phase, either of which can be continuous. These products are in most cases both dispersions and emulsions, in that they often contain a continuous liquid phase, a dispersed liquid phase, and a dispersed solid phase. The pigment can be dispersed into either phase, although it is more typically dispersed into at least the continuous phase. Water can constitute 30 to 75% of the weight of a wet foundation product. Pigments generally constitute from 2 to 25% by weight of a wet foundation. Emollients can constitute from 1 to 35% by weight of a wet foundation. A surfactant is often present in an amount from 0.1 to 15% by weight. The alkyl ketal ester can constitute from 0.5 to 35% by weight of a wet foundation. Other ingredients can include, for example, thickeners, preservatives, cosolvents, and the like.

A fluid or gel eyeliner typically contains from 25 to 80% by weight of water and/or one or more volatile organic solvents, from 2 to 35% of a wax, film-forming polymer, and/or emollient, from 2 to 30% by weight of the pigment, and from 1 to 40%, or 25% by weight of the alkyl ketal ester.

These products are often both emulsions and dispersions. This type of product can also contain one or more thickeners or gelling agents, one or more surfactants or cosolvents that can function as a stabilizer for the emulsified wax, film-forming polymer, and/or emollients. They can also contain other ingredients, such as preservatives.

A mascara product can be, for example, an oil-in-water emulsion, a water-in-oil emulsion, or an anhydrous organic formulation, in each case containing dispersed pigment particles. A mascara product typically contains one or more waxes or film-forming polymers. They can also contain one or more emollients, thickeners, surfactants, or cosolvents (which can serve as stabilizer for the emulsified wax or film-forming polymer), preservatives, or other ingredients. A mascara product can contain from 1 to 25% by weight of dispersed pigment particles, from 5 to 50% by weight of a wax and/or film-forming polymer, from 25 to 75% by weight of water and/or organic solvent, and from 1 to 50%, or from 1 to 25% by weight of the alkyl ketal ester.

Lip care product such as lipsticks and lip glosses are typically in stick form or in the form of a thick liquids or pastes. Many lip care products include a mixture of one or more waxes with one or more oils and, in the case of lipsticks at least, one or more pigments. It is understood that those skilled in the art can design the stick formulations to have the proper stick stability and product delivery (deposition of color on the lips, for instance) through proper selection of wax blends and other ingredients. These products are normally characterized as being anhydrous. A lip care product formulation can contain, for example, from 1 to 25%, or 20% by weight of a wax; from 30%, or from 50 to 95% by weight of one or more other hydrophobic materials, of which castor oil is often an important component especially in lipsticks; from 0.051 to 25%, or 10% by weight of one or more pigments, more typically at least 1% in the case of lipsticks, and from 1 to 50%, or from 1 to 25% by weight of the alkyl ketal ester.

Cosmetic products such as those described, in which the pigment or other particles are dispersed in a carrier (the liquid or semi-solid continuous phase), can be prepared in several ways. The particles can be wetted with the alkyl ketal ester, prior to dispersing them into the carrier. Alternatively (or in addition), the alkyl ketal ester can be blended into the carrier prior to dispersing the pigment or particles into it, or the components can be combined simultaneously.

A wide variety of carriers can be used in the cosmetic formulations and products, depending on the end use of the cosmetic and the desired characteristics. Generally, the carrier includes at least one (a) paraffinic, naphthenic or aromatic mineral oil, (b) nonionic organic compounds which has a melting temperature of less than 45° C., has a molecular weight of at least 190, contains at least one amido, or ester group and at least one alkyl chain containing at least 8 carbon atoms, and has a solubility in water of no greater than 1 part in 99 parts of water; (c) nonionic organosilicone compound which has a melting temperature of less than 45° C. and has a solubility in water of no greater than 1 part in 99 parts of water; (d) long chain alcohol, (e) wax, or (f) film-forming polymer. At least one alkyl ketal ester is present in the carrier, or sorbed onto or into the solid pigment particles, or both. The specific ingredients and relative proportions of the foregoing ingredients will depend on the form of the specific cosmetic product. An eyeliner, for example, can take the form of a somewhat viscous fluid or gel, or can be a malleable stick product. An eyeliner generally contains (1) at least one wax or at least one film-forming polymer or (2) at least one emollient, or both (1) and (2), together with (3) at least one dispersed pigment. In stick and pencil products, the wax, film-forming polymer, and/or emollient can constitute, in the aggregate, from 25 to 80% of the total weight of the product, the pigments can constitute from 5 to 50% of the weight of the product, and the alkyl ketal ester can constitute from 0.1 to 50%, 25%, or 10% of the weight of the product. Stick-type products typically contain no more than 10% by weight of water.

Components (a) include paraffinic, naphthenic, or aromatic mineral oils. These materials are often present as all or part of an oil phase in emulsion formulations such as certain lotions and creams. They often function as emollients that soften the skin upon application.

Useful component (b) materials include a wide range of vegetable oils and animal oils. Oils which have a required HLB of at least 6, or at least 7, tend to dissolve more easily in the alkyl ketal esters and are preferred in cases in which the alkyl ketal ester is to reside at least partially in an oily phase, or in which the alkyl ketal ester is to dissolve or be dissolved into the oil.

Other useful component (b) materials include, for example, $C_{8-24}$ linear or branched alkyl esters of $C_{8-24}$ fatty acids, di-$C_{8-24}$ esters of dicarboxylic acids, $C_{8-24}$ fatty acid esters of $C_{8-24}$ linear or branched alkanoic acids, $C_{8-24}$, especially $C_{12-15}$ alkyl benzoates, poly(propylene oxide) esters of $C_{8-24}$ fatty acids, di-$C_{8-24}$ linear or branched alkyl esters of aromatic diacids, di-$C_{8-24}$ fatty acid esters of aromatic diacids, and the like. Other useful component (b) materials include, for example, $C_{8-24}$ linear or branched alkyl amides of $C_{8-24}$ fatty acids, di-$C_{8-24}$ amides of dicarboxylic acids, $C_{8-24}$ fatty acid amides of $C_{8-24}$ linear or branched alkanoic acids, poly(propylene oxide) amides of C8-24 fatty acids, di-$C_{8-24}$ linear or branched alkyl amides of aromatic diacids, di-$C_{8-24}$ fatty acid amides of aromatic diacids, and the like.

Examples of the component (c) materials are dimethicone and cyclopentasiloxane.

The component (d) materials are long chain (eight or more carbon atoms) alcohols such as 1-octanol, 1-decanol, 1-docecanol, cetyl alcohol, and the like.

Suitable waxes include synthetic or mineral waxes such as ceresin, montan, ozocerite, peat, paraffin, microcrystalline, polypropylene and other polymerized poly-α-olefin waxes, substituted amide, petroleum jelly, esterified or saponified waxes, and the like; and waxes of plant or animal origin including beeswax, chinese wax, lanolin, shellac wax, spermaceti, bayberry, candelilla, carnauba, castor, esparto, Japan, ouricury, rice bran or soy waxes.

Among the useful film-forming polymers (component (f)) are corn starch (modified), acrylates/octylacrylamide copolymer, polyurethane-14 and AMP-acrylates copolymer, hydrolyzed wheat protein, polyvinylpyridine (PVP), hydrolyzed wheat protein/PVP crosspolymer, vinyl acetate/crotonates/vinyl neodecanoate copolymers, potassium butyl ester of PVM/MA copolymer, polyurethane-14 & AMP-acrylates copolymer, isobutylene/ethyl maleimide/hydroxylethylmaleimide copolymer, polyvinylpyrrolidone/vinyl acetate polymers, acrylates/hydroxyesters acrylates copolymer, polyurethanes, polyvinyl methyl ester/maleate, octylacrylamide/acrylates/butylaminoethyl methacrylate copolymer, nitrocellulose, cellulose acetate propionate, cellulose acetate butyrate, styrene/acrylates copolymers, acrylates copolymers and polyethylene terepthalate and the like.

A composition can include a surfactant, which can include ionic (cationic, anionic, or zwitterionic) compounds that contain a hydrocarbon group of at least 8 carbon atoms. The hydrocarbon group preferably includes at least one alkyl group having at least 8 carbon atoms. The ionic surfactants include, for example, anionic surfactants which include one or more sulfate, sulfonate or phosphate groups, which are in the neutralized (or "salt") form; cationic surfactants which include one or more quaternary ammonium or quaternary phosphonium groups, which are in the neutralized (or "salt") form; one or more zwitterionic groups which can, depending on the pH of the product, assume either an anionic or cationic form (as with the betaines, for example), or can assume a cationic or nonionic form (as with the amine oxide surfactants, for example). The emulsifier may be generated in-situ, for example, when stearic acid is added to the oil phase, and triethanol amine is added to the water phase and the TEA-stearate salt forms when the oil and water phases are mixed.

The cosmetics can, of course, contain any of a wide range of other ingredients as needed or desired for a particular end-use application.

In another aspect, this invention is a particulate organic, inorganic, or inorganic-organic solid in which the particles are at least partially coated with an alkyl ketal ester I. The alkyl ketal ester can, in this aspect, function as a slip agent (by lubricating the particles) and/or as a dispersing aid. The alkyl ketal ester is present in an amount effective to perform the desired function, for example from 0.1 to 100%, from 0.1 to 50%, from 1 to 30%, or from 1 to 10% by weight of the particulate solid. It is to be understood that the term "coated" as used herein includes embodiments where the alkyl ketal ester is at least partially absorbed into the particles.

The at least partially coated particles can be used in the dispersions described above, i.e., as the particulate phase dispersed in a liquid or semi-solid continuous phase. The at least partially coated particles can be easily dispersed into a variety of fluids due to the presence of the alkyl ketal esters, which renders the surface of the particles compatible with those fluids. In other embodiments, the at least partially coated particles are used in the manufacture of dry compositions, for example in the form of a dry or nearly dry powder, an oily powder, or a paste, depending on the amount of alkyl ketal ester present. As used herein "dry" compositions are distinguished from the above-described dispersions by the lack of a liquid or semi-solid continuous phase.

A variety of solids as described above can be used as the particulates in these embodiments. In an aspect, the solid particulate is a solid pigment as described above. A solid inorganic pigment can be particularly mentioned. As described above, the at least partially coated solid pigment can be easily dispersed into a variety of liquid and semi-solid, aqueous and non-aqueous systems, and thus can be easily incorporated into various products such as paints, inks and cosmetics of the type described before. The cosmetics contain the particulate solids at least partially coated with alkyl ketal ester I and an ingredient (a)-(f) or a combination thereof.

In other embodiments, the at least partially coated pigments are used in the manufacture of dry compositions, for example in the form of a dry or nearly dry powder, an oily powder, or a paste, depending on the amount of alkyl ketal ester present. The at least partially coated pigments can be useful as, for example, a dry pigment, toner, or powder coating. The alkyl ketal ester I can constitute from 0.1 to 100%, from 0.1 to 50%, from 1 to 30%, or from 1 to 10% by weight of the particulate pigment.

The at least partially coated pigment particles, in particular at least partially coated inorganic pigment particles, can be useful in dry cosmetic formulations and products. (Of course, other solid particulates at least partially coated with alkyl ketal ester I, such as silica, can also be used). In an embodiment, a powder cosmetic comprises a solid pigment and an alkyl ketal ester I. Such a cosmetic can be, for example, a powder color cosmetic product, a powder cream cosmetic product, a pressed powder color cosmetic product, a blush, or an eye shadow.

In another aspect, a solid pigment having at least one alkyl ketal ester sorbed onto or into the solid pigment particles is described. Blushes, pressed powder eye shadows, and dry foundations are examples of such pigment compositions. Blushes, pressed powder eye shadows, and dry foundations are typically powders, which can be free-flowing or somewhat caked. In these powder products, the pigment(s) typically constitute from 50 to 95% by weight of the product. The alkyl ketal ester can constitute from 0.1 to 15%, from 1 to 12%, or from 1 to 10% by weight of the product. Other filler particles can be present in amounts from 1 to 95% by weight of the product. In a powder cream, the alkyl ketal ester can constitute from 0.1 to 40%, from 1 to 30%, or from 1 to 20% by weight of the product, optionally together with other filler particles, which can be present in amounts from 1 to 95% by weight of the powder cream product. The alkyl ketal esters I can function in these products as a slip agent that allows the particles to adhere slightly yet spread easily upon application. Emollients can be present in an amount, for example, of from 1 to 25% by weight of the product. Preservative, film-forming polymer and other optional ingredients can be present. These products typically contain no more than 1% by weight of water, and can contain water scavengers to prevent caking.

The solid particulates at least partially coated with alkyl ketal ester I also can be incorporated into various organic polymers, to produce, for example, pigmented polymers and/or filled or reinforced polymers. The at least partially coated solid particulates can also be used as colorants for color filters for flat panels displays, not only for additive but also for subtractive color production; coloration of macromolecular materials of any kind, for example natural and synthetic fiber materials, for example cellulose fibers; for paper pulp coloration; laminate coloration; textile printing colors; wallpaper colors, viscose dope dyeing systems; powder coatings; sausage casings; coloration of seed, fertilizers, glass, particularly glass bottles, roof shingles, renders, concrete, wood stains, colored pencil leads, chalks, waxes, paraffins, shoe care agents, latex products, abrasives, photoresists, floor and car waxes, crayons, coatings for foods (such as wax coatings for cheeses), leather polishes, nail polishes, and as colorants for "electronic inks" ("e-inks") and "electronic paper" ("e-paper").

The solid particulates at least partially coated with alkyl ketal ester I are also useful as a colorant in electrophotographic toners and developers, for example in one- or two-component powder toners (also called one- or two-component developers), magnet toners, liquid toners, latex toners, polymerization toners and also specialty toners. Typical toner binders in this context are addition polymerization resins, polyaddition resins and polycondensation resins, such as styrene, styrene-acrylate, styrene-butadiene, acrylate, polyester, phenol-epoxy resins, polysulfones, polyurethanes, individually or in combination, and also polyethylene and polypropylene, which may each contain further ingredients, such as charge control agents, waxes or flow assistants, or are subsequently modified with these adjuvants.

Use of the alkyl ketal esters allows excellent dispersion of solid particles in liquid and semi-solid phases. The performance of the products containing the dispersions can have enhanced performance due to the characteristics of the dispersion, e.g., the targeted viscosity, and the uniformity of the dispersion. The dispersions can be stable over time (e.g., one week, one month, six months, one year, or even longer).

Use of the alkyl ketal esters can also improve the ability to form the dispersions, as well as the stability of those dispersions. These characteristics are influenced by factors such as the affinity of the particle surfaces to the dispersing medium and the density of the particles relative to the density of the dispersing medium. In general, particles become harder to disperse and harder to maintain in dispersion as their surfaces become less compatible with the dispersing medium and as the difference in density between particles and dispersing medium becomes greater. Without being bound by theory, it is believed that the alkyl ketal esters described herein can function as a compatibilizer between the particles and the dispersing medium. The differing solubilities of the alkyl ketal esters allows selection of the appropriate ester depending on the particular solid and dispersing medium. Formulation of various dispersions is therefore simplified, as the number of dispersants to be tested is decreased for a given formulation. In cases where a fully water-miscible ketal or a partially water-miscible is used to make the pigmented compositions or concentrates, the equipment can be quickly or easily cleaned with water, which has the advantage of being low-odor and environmentally friendly. In the case where a fully alcohol miscible ketal or a partially alcohol-miscible ketal is used, the equipment can be quickly or easily cleaned with alcohol, avoiding or minimizing the use of malodorous hydrocarbon solvents. The alkyl ketal ester has the additional advantage of being bio-based, and may serve additional functions in the formulation, such as an emollient, a coalescent, or a cosolvent.

The following examples are being provided to illustrate the invention but not to limit the scope thereof. All parts and percentages are by weight unless otherwise indicated.

EXAMPLES

Example 1a

Titanium Dioxide Particles Dispersed in Ethyl-LGK

Titanium dioxide particles (T-Lite SF from BASF, containing titanium dioxide, aluminum hydroxide, and Dimethicone/Methicone Copolymer) were separately dispersed in ethyl-LGK and in caprylic/capric triglyceride at a 37/63 weight ratio, using a Silverson high shear mixer until the dispersion was no longer flowable. The dispersions were held for 24 hours, and their viscosities then measured on a Brookfield viscometer model RVT at 5 rpm with a TD spindle. The viscosity of the caprylic/capric triglyceride dispersion was $1.20 \times 10^5$ cP; whereas that of the ethyl-LGK dispersion was $1.88 \times 10^5$ cP. The similar viscosities of these dispersions show that ethyl-LGK is approximately as effective a dispersant as the conventional triglyceride pigment dispersant.

Example 1b

Zinc Oxide Particles Dispersed in Ethyl-LGK

In the same manner, 40 parts of zinc oxide (Z-Cote HP1 from BASF, containing zinc oxide triethoxycaprylylsilane) are separately dispersed into each of the same two dispersants. The viscosity of the caprylic/capric triglyceride dispersion is $0.44 \times 10^5$ cP; whereas that of the ethyl-LGK dispersion is $1.4 \times 10^5$ cP. The similar viscosities of these dispersions again indicate that ethyl-LGK is approximately as effective a dispersant as the conventional triglyceride pigment dispersant.

Example 2

Carbon Black Absorption

The ability of carbon black to absorb ethyl-LGK, ethyl-LPK, and diisobutyl phthalate was determined according to ASTM D1483. Carbon black absorbed about 151 g of ethyl-LGK and 169 g of ethyl-LPK per 100 grams of pigment; this was comparable to 180 g of dioctyl phthalate which was absorbed by an equivalent weight of carbon black.

Example 3

Method of Forming a Dispersion with Ethyl-LPK and Butyl-LGK

Using an overhead mixer with a Cowles blade, Ti-pure R960 titanium dioxide (E.I. Du Pont de Nemours) was slowly added to the solvent shown in Table 1, mixing between additions until the viscosity was uniform. After additional mixing for the reported period of time, the dispersion quality was measured on a Hegman grind block. Additional solvent was added to obtain a mixture of a pourable viscosity (total amount of solvent reported in the table).

TABLE 1

| Ex. | Solvent | Pigment (wt.%) | Solvent (wt.%) | Mix Speed (rpm) | Mix Time (min) | Dispersion Quality (microns) | 24 Hour Observation |
|---|---|---|---|---|---|---|---|
| | | | Hydroxyl solvents | | | | |
| 3A | Butyl Cellosolve[1] | 50 | 50 | 600 | 2 | 0 | separation |
| 3B | Ethyl LGK | 50 | 50 | 600 | 2 | 0 | homogeneous |
| 3C | Butyl LGK | 50 | 50 | 600 | 3 | 0 | homogeneous |
| | | | Non-hydroxyl solvents | | | | |
| 3D | DPM Acetate[1] | 40 | 60 | 800 | 3 | 10 | separation |
| 3E | Ethyl LPK | 40 | 60 | 800 | 3 | 10 | slight separation |

[1] The Dow Chemical Company

The results in Table 1 shown that after allowing the dispersions were stored overnight without stirring, the Ethyl-LGK and Butyl-LGK pigment dispersions were stable and homogeneous, while the Butyl Cellosolve mixture had separated. The Ethyl LPK and the DPM acetate mixtures both separated, but the DPM acetate had separated to a greater extent.

Example 4

Method of Forming a Dispersion with Ethyl-LGK

Using an overhead mixer with a Cowles blade, Heliogen L6905F Blue (BASF) or SR730 Carbon Black (Sid Richardson) as shown in Table 2 were slowly added to Ethyl-LGK solvent, mixing between additions until the viscosity was uniform. A measured amount of media sand was added and the mixture was further dispersed using the overhead mixer with a disc blade at the specified RPM until an acceptable dispersion level on the Hegman grind block was met. Additional solvent was added to achieve a pourable viscosity (total solvent used shown in table 2), and the mixture was poured through a 100 micron filter to remove the sand. The dispersions were then stored overnight.

TABLE 2

| Ex. | Pigment | Pigment (g) | Solvent (g) | Resin (g) | Sand (g) | Mix Speed (rpm) | Mix Time (min) | Dispersion Quality (microns) | 24 Hour Observation |
|---|---|---|---|---|---|---|---|---|---|
| 4A | SR730 Black | 20 | 80 | 0 | 60 | 2500 | 4 | 0 | slight separation |
| 4B | L6905F Blue | 20 | 80 | 0 | 75 | 2500 | 20 | 30 | slight separation |
| 4C | L6905F Blue | 20 | 80 | 25 | 75 | 2500 | 15 | 20 | slight separation |

After storing the dispersions overnight without stirring, the dispersions with SR730 Carbon black and Heliogen Blue L6905F showed slight separation. Addition of Duramac HS-207-2012 resin to the pigment dispersion (Ex. 7C) yielded no improvement in dispersion stability.

Example 5

Method of Forming a Dispersion with Ethyl-LGK

Using an overhead mixer with a Cowles blade, Iron Oxide Red HR-1203 (Hoover Color) was slowly added to Ethyl LGK solvent, mixing between additions until the viscosity was uniform. A measured amount of media sand was added and the mixture was further dispersed using the overhead mixer with a disc blade at the specified RPM until an acceptable dispersion level on the Hegman grind block was met. Additional solvent was added to achieve a pourable viscosity as shown in Table 3, and the mixture was poured through a 100 micron filter to remove the sand.

TABLE 3

| Ex. | Pigment (g) | Solvent (g) | Sand (g) | Mix Speed (rpm) | Mix Time (min) | Dispersion Quality (microns) | 24 Hour Observation |
|---|---|---|---|---|---|---|---|
| 5A | 300 | 300 | 300 | 3000 | 5 | 0 | homogeneous |

After allowing the dispersions to sit overnight, the dispersion with HR-1203 Iron Oxide Red HR-1203 showed no settling.

The final dispersion of 5A was then further dispersed into different resin systems as shown in Table 4 using a paddle blade on an overhead mixer (Ex. 5B-E) and viscosities were measured with a Brookfield viscometer. Results are shown in Table 4. The "-" indicates that the composition was not further processed.

TABLE 4

| Ex. | Amount of 5A (g) | Resin | Resin (g) | Mix Time (min) | Viscosity 1.5 rpm (spindle) | Dispersion Quality (microns) | 24 Hour Observation |
|---|---|---|---|---|---|---|---|
| 8A | — | — | — | — | 16833 (5) | — | — |
| 8B | 170 | Joncryl 500 | 42.5 | 5 | 5067 (3) | 7.5 | — |
| 8C | 170 | Joncryl 500 | 113.3 | 5 | 2133 (3) | 7.5 | slight separation |
| 8D | 170 | Duramac HS207-2012 | 42.5 | 5 | 3867 (3) | 7.5 | — |
| 8E | 170 | Duramac HS207-2012 | 113.3 | 5 | 2133 (3) | 7.5 | slight separation |

These results showed that the pre-dispersion can be used to further disperse the pigment into different resin systems.

Example 6

Method of Forming a Dispersion with Ethyl-LPK

Using an overhead mixer with a Cowles blade, Ti-pure R960 titanium dioxide (DuPont) was slowly added to solvent as shown in Table 5, mixing between additions until the viscosity was uniform. After additional mixing for the reported period of time, the dispersion quality was measured on a Hegman grind block. Additional solvent (amount not reported) was added to achieve a pourable viscosity, and the viscosity of the dispersion was measured on a Brookfield viscometer.

TABLE 5

| Ex. | Solvent | Pigment (g) | Solvent (g) | Mix Speed (rpm) | Mix Time (min) | Dispersion Quality | 24 Hour Observation |
|---|---|---|---|---|---|---|---|
| 6A | DPM Acetate | 200 | 300 | 800 | 3 | 7.5 | heavy separation |
| 6B | Ethyl LPK | 200 | 300 | 800 | 3 | 7.5 | slight separation |

After allowing the dispersions to store overnight, the Ethyl-LPK pigment dispersion had slight separation while the DPM acetate mixture had heavy separation.

The final dispersions 6A-B were further dispersed into different resin systems and the viscosity was measured as shown in Tables 6, respectively.

TABLE 6

| Ex. | Amount of 6A (g) | Resin | Resin (g) | Mix Time (min) | Viscosity 1.5 rpm (spindle) | Dispersion Quality | 24 Hour Observation |
|---|---|---|---|---|---|---|---|
| 6A1 | — | — | — | — | 50667 (5) | — | — |
| 6A2 | 170 | Joncryl 500 | 42.5 | 5 | 400 (3) | 7.5 | — |
| 6A3 | 170 | Joncryl 500 | 113.3 | 5 | 200 (3) | 7.5 | heavy separation |
| 6A4 | 170 | Duramac HS207-2012 | 42.5 | 5 | 67 (3) | 7.5 | — |
| 6A5 | 170 | Duramac HS207-2012 | 113.3 | 5 | 67 (3) | 7.5 | slight separation |
| 6B1 | — | — | — | — | 49867 (5) | — | — |
| 6B2 | 170 | Joncryl 500 | 42.5 | 5 | 467 (3) | 7.5 | — |
| 6B3 | 170 | Joncryl 500 | 113.3 | 5 | 267 (3) | 7.5 | separation |
| 6B4 | 170 | Duramac HS207-2012 | 42.5 | 5 | 67 (3) | 7.5 | — |
| 6B5 | 170 | Duramac HS207-2012 | 113.3 | 5 | 133 (3) | 7.5 | slight separation |

After allowing the dispersions to sit overnight, the Ethyl LPK pigment dispersion had slight to moderate separation while the DPM acetate mixture had slight to heavy separation.

Examples 7-9

Preparation of Pigment Concentrate

Example 7-9 used an 80% NV acrylic resin dispersant often used with carbon black, and a solvent commonly used to assist in viscosity reduction of the grind base and to facilitate in pigment wetting. The solvent chosen to serve as a Standard for comparison (Comparative Example 7) was PM Acetate.

To prepare Examples 10-12, all ingredients of each pigment concentrate were blended together with light mixing and then loaded into a steel ball mill, Table 11. After 30 minutes of milling, the viscosity of the pigment concentrates of Examples 8 and 9 were too high to disperse the lamp black. To lower the viscosity of these concentrates, it was necessary to increase the PM acetate of the Standard by 16.7% to achieve pigment concentrates that would allow for sufficient milling to disperse the lamp black pigment. The adjusted mill bases were then dispersed in the steel ball mills for 12 hours. Results are shown in Table 7.

TABLE 7

| Ingredient | 7 | 8 | 9 |
|---|---|---|---|
| Joncryl 920 acrylic resin: | | | |
| Solids | 27 | 27 | 27 |
| Volatile (MAK) | 6.7 | 6.7 | 6.7 |
| BYK 108 pigment dispersant | 2.2 | 2.2 | 2.2 |
| LB1011 lamp black | 21.5 | 21.5 | 21.5 |
| PM acetate | 42.6 | 0 | 0 |
| Et-LGK | 0 | 42.6 | 0 |
| Et-LPK | 0 | 0 | 42.6 |
| Test Results | | | |
| Total solids content (wt. %) | | | |
| Theoretical | 50.69 | 46.70 | 46.70 |
| Actual (ASTM D2369) | 51.00 | 55.56 | 47.13 |
| Total volatile content (wt. %) | | | |
| Theoretical | 49.31 | 53.30 | 53.30 |
| Actual (ASTM D2369) | 49.00 | 44.44 | 52.86 |
| Viscosity (Kreb units) | 100 | 140 | 103 |
| Shear Thinning Profile (cps): | | | |
| 10 RPM | 17,000 | 48,400 | 16,880 |
| 20 RPM | 9,600 | 25,000 | 9,820 |
| 50 RPM | 4,688 | 13,680 | 4,888 |
| 100 RPM | 2,800 | 8,960 | 3,012 |
| Hegman Fineess of Grind | 8 N.S. | 8 N.S. | 8 N.S. |

[1]Assumes that the Segetis solvent is 100% volatile

After each mixture was milled for 12 hours, the Hegman fineness of grind was checked on all samples. All were found to be ground to an 8 N.S. At this point, each was evaluated for the base viscosity and shear-thinning characteristics. The alkyl ketal esters tested were sufficient to act as a replacement for the PM acetate and to achieve the expected Hegman grind of 7-8 N.S. However, as noted, it was necessary to increase the solvent level with these green solvents to reduce the mill base viscosity. This is due to the lower solubility of the acrylic/pigment mixture in the green solvents relative to the PM acetate. The viscosity of the Et-LGK green solvent containing pigment concentrate yielded a dispersed mixture that was significantly higher than the Standard. However, the Et-LPK produced low and high shear viscosities very comparable with that of the PM acetate-containing Standard.

When a thin film was cast using the Standard pigment concentrate dried, it dried down to a flat black within 15 minutes. The Et-LGK did not dry, but remained mobile, glossy film even after 4 days at room temperature. The Et-LPK-containing concentrate did eventually dry down to a flat black with 24-36 hours.

Determination of the actual VOC of each of these pigment concentrates showed that the only concentrate to retain any significant amount of the solvent was prepared with the Et-LGK. This coating retained 18.81% of this green solvent. In contrast, the concentrate containing the Et-LPK retained only 0.6% of this solvent. However, with the use of the Et-LPK, the VOC of the concentrate was 522.82 g/l, while the Standard concentrate had a VOC of 537.43 g/l as per ASTM D3960. The actual VOC of the concentrate with SG-22000D was 593.86 g/l.

The impact of slow dry or lack of dry of the green solvent in the pigment concentrate should not be expected to have an serious impact on the speed of dry of the tinted coating given the low level at which such concentrates are typically used.

Example 10

Solvent-Based InkJet Ink

A pigment dispersion as shown in Table 8 is prepared by introducing a pigment and a dispersant into a solvent, stirring the mixture with a high-speed mixer until the mixture became homogeneous, and then dispersing the resulting mill base with a horizontal sand mill for about two hours. The inkjet ink is then prepared by mixing the pigment dispersion with the remaining resin, a surface conditioning agent, and a solvent. The final mixture is filtered through a polypropylene 1 micrometer filter to produce the final ink.

TABLE 8

| Ingredient | Function | Parts by wt. |
|---|---|---|
| Pigment Dispersion | | |
| Lionol Blue FG-7400-G (Toyo Ink) | Pigment | 40.0 |
| Ajisper PB821 (Ajinomoto Fine-Techno) | Dispersant | 14.0 |
| Ethyl LGK | Solvent | 46.0 |
| Inkjet Ink | | |
| <See above> | Pigment Dispersion | 10.8 |
| VYHD (Dow) | Resin | 6.5 |
| BYK-361N | Surface conditioner | 0.5 |
| Ethyl LPK | Solvent | 82.2 |

Example 11

Water Based Latex Interior Paint

The pigment grind as shown in Table 9 is prepared by introducing the ingredients in the order listed and stirring the mixture with a high-speed mixer until the mixture became homogeneous. Once all ingredients are added, the homogenous mixture is then dispersed with a horizontal sand mill for about twelve hours. The paint is prepared by mixing the pigment grind with the Letdown mixture containing a resin, coalescent, and other additives with a high-speed mixer until homogeneous.

TABLE 9

| Ingredient | Function | Parts by wt. |
|---|---|---|
| Pigment Grind | | |
| Water | Diluent | 184.0 |
| Propylene glycol | Diluent/antifreeze | 26.0 |
| Tamol 1124 (Dow) | Dispersant | 9.0 |
| Triton X-405 (Dow) | Surfactant | 2.0 |
| Rhodoline 643 (Rhodia) | Antifoam | 1.5 |
| AMP-95 (Dow/Angus) | PH stabilizer | 2.0 |
| Ti-Pure R-900 (Dupont) | Pigment | 100.0 |
| Anhydrous aluminum silicate | Pigment | 150.0 |
| Calcium carbonate | Pigment | 190.0 |
| Letdown | | |
| UCAR latex 379G (Arkema) | Resin | 254.0 |
| Ethyl-LPK | Coalescent | 16.0 |
| Rhodoline 643 (Rhodia) | Antifoam | 2.5 |
| Water | Diluent | 60.3 |
| UCAR Polyphobe 102 (Arkema) | Thickener | 12.5 |
| Water | Diluent | 119.2 |

Examples 12-18

Lipsticks Containing Water

A lipstick was prepared from the ingredients of Table 10. The ingredients designated as "A" were combined and heated to 80-85° C. until melted and clear. The ingredients designated as "B" were mixed and ground together and then mixed into the melted phase "A" materials. When the mixture appears uniform, the temperature was dropped to 75° C. The ingredients designated as "C" were mixed together and then added to the melted phase "A" and "B" materials until homogenous. This lipstick contained 1% by weight water, yet remained stable upon storage.

TABLE 10

| Ingredients | wt. % |
|---|---|
| Part A | |
| Caprylic/capric triglyceride | 8.56 |
| Octyldodecyl stearoyl stearate | 13.37 |
| Triisostearyl citrate | 4.05 |
| Pentaerythrityl citrate | 5.60 |
| Jojoba esters | 1.72 |
| Lanolin oil | 1.62 |
| Bis-diglyceryl polyacryladipate-2 | 1.02 |
| Castor oil | 30.50 |
| Carnauba wax | 2.30 |
| Candelilla wax | 5.24 |
| Beeswax | 2.09 |
| Ozokerite wax | 1.80 |
| Microcrystalline wax | 1.13 |

TABLE 10-continued

| Ingredients | wt. % |
|---|---|
| Phenoxyethanol | 1.00 |
| Polyethylene | 1.00 |
| Octyl methoxy cinnamate | 0.60 |
| Tocopheryl acetate | 0.05 |
| Part B | |
| Castor oil | 10.00 |
| D&C red no. 6 | 6.25 |
| Iron oxide | 0.10 |
| Part C | |
| 50% mixture of Et-LGK & purified water | 2.00 |

Lipsticks were prepared from the ingredients in Table 12.

TABLE 12

| Ingredient | 13 | 14 | 15 | 16 | 17 | 18 |
|---|---|---|---|---|---|---|
| Part A | | | | | | |
| Caprylic/Capric Triglyceride | 8.56 | 8.56 | 8.56 | 8.56 | 8.56 | 8.56 |
| Octyldodecyl Stearoyl Stearate | 13.37 | 13.37 | 13.37 | 13.37 | 13.37 | 13.37 |
| Triisostearyl Citrate | 4.05 | 4.05 | 4.05 | 4.05 | 4.05 | 4.05 |
| Pentaerythrityl Tetraisostearate | 5.60 | 5.60 | 5.60 | 5.60 | 5.60 | 5.60 |
| Jojoba Esters | 1.72 | 1.72 | 1.72 | 1.72 | 1.72 | 1.72 |
| Lanolin Oil | 1.62 | 1.62 | 1.62 | 1.62 | 1.62 | 1.62 |
| Bis-Diglyceryl Polyacyladipate-2 | 1.02 | 1.02 | 1.02 | 1.02 | 1.02 | 1.02 |
| Copernicia Cerifera (Carnauba) Wax | 2.30 | 2.30 | 2.30 | 2.30 | 2.30 | 2.30 |
| Euphorbia Cerifera (Candelilla) Wax | 5.24 | 5.24 | 5.24 | 5.24 | 5.24 | 5.24 |
| Ricinus Communis (Castor) Seed Oil | 10.50 | 10.50 | 10.50 | 10.50 | 10.50 | 10.50 |
| Cera Alba (Beeswax) | 2.09 | 2.09 | 2.09 | 2.09 | 2.09 | 2.09 |
| Ozokerite Wax | 1.80 | 1.80 | 1.80 | 1.80 | 1.80 | 1.80 |
| Microcrystalline Wax | 1.13 | 1.13 | 1.13 | 1.13 | 1.13 | 1.13 |
| Phenoxyethanol | 1.00 | 1.00 | 1.00 | 1.00 | 1.00 | 1.00 |
| Polyethylene | 1.00 | 1.00 | 1.00 | 1.00 | 1.00 | 1.00 |
| Octyl Methoxycinnamate | 0.60 | 0.60 | 0.60 | 0.60 | 0.60 | 0.60 |
| Tocopheryl Acetate | 0.05 | 0.05 | 0.05 | 0.05 | 0.05 | 0.05 |
| Part B | | | | | | |
| Ricinus Communis (Castor) Seed Oil | 18.00 | 16.00 | 14.00 | 12.00 | 10.00 | 2.00 |
| Part C | | | | | | |
| Ricinus Communis (Castor) Seed Oil | 10.00 | 10.00 | 10.00 | 10.00 | 10.00 | 10.00 |
| D&C Red No. 6 Barium Lake | 6.25 | 6.25 | 6.25 | 6.25 | 6.25 | 6.25 |
| Iron Oxide | 0.10 | 0.10 | 0.10 | 0.10 | 0.10 | 0.10 |
| Part D | | | | | | |
| 50% mixture of Et-LGK and Purified Water | 4.00 | 6.00 | 8.00 | 10.00 | 12.00 | 20.00 |

To prepare the lipsticks, Part A was heated at 80-85° C. with mixing. When Part A was completely melted and clear, Part B was added to Part A while mixing. Part C was pre-ground. When Part A/B was completely melted and clear, Part C color grind was added to the combined Parts A and B. When all the color was dispersed and the batch was uniform, the batch temperature was dropped to 75° C. and the Part D solution was slowly added to the batch with mixing. The batch was mixed until completely homogeneous. When the batch was uniform, it was poured into molds to cool.

Alternatively, Part D can be added to combined Parts A and B before addition of Part C, though care should be taken to avoid or minimize water loss.

The lipstick structure was good in each of Examples 16-22. Samples were aged at 45° C. for 4 weeks to determine stability, and it was found that none of the sticks sweated, showed signs of condensation, or softened when returned to room temperature. There were further no signs of color bleed or color change.

Water content was verified for Examples 13-18 as follows. Lipsticks were dried in a vacuum oven at 35° C. for 24 hours and the weight loss was monitored. The observed mass loss was consistent with the weight loss expected from evaporation of the charged mass of water in the lipstick. Results are shown in Table 12.

TABLE 12

| Lipstick Example | Charged water (wt. %) | Mass Loss (wt. %) | % of expected |
|---|---|---|---|
| 13 | 2 | 1.16 | 57.9 |
| 14 | 3 | 3.1 | 103 |
| 15 | 4 | 3.4 | 84.9 |
| 16 | 5 | 4.9 | 97.9 |
| 17 | 6 | 6.6 | 110 |
| 18 | 10 | 10.6 | 106 |

Examples 19-23

Preparation of Candles with Natural Waxes

Candles with natural waxes were prepared from the ingredients in Table 13.

TABLE 13

| Ingredient | 19 wt. % | 20 wt. % | 21 wt. % | 22 wt. % | 23 wt. % |
|---|---|---|---|---|---|
| Part A | | | | | |
| Nature wax P-1 | 0 | 0 | 0 | 0 | 0 |
| Nature wax C-1 | 29.93 | 29.93 | 29.93 | 29.93 | 31.50 |
| Nature wax C-3 | 29.93 | 29.93 | 29.93 | 29.93 | 31.50 |
| Beeswax | 29.93 | 29.93 | 29.93 | 29.93 | 31.50 |
| Part B | | | | | |
| Cinqasia red B RT-195-1 | 0.23 | 0.23 | 0.23 | 0.23 | 0.24 |
| Et-LGK | 0 | 0 | 0 | 0 | 5.25 |

TABLE 13-continued

| Ingredient | 19 wt. % | 20 wt. % | 21 wt. % | 22 wt. % | 23 wt. % |
|---|---|---|---|---|---|
| Part C | | | | | |
| Et-LGK | 4.99 | 0 | 0 | 0 | 0 |
| Bu-LGK | 0 | 0 | 4.99 | 4.99 | 0 |
| Et-LPK | 0 | 4.99 | 0 | 0 | 0 |
| Bergamot (*Citrus bergamia*) essential oil | 0 | 0 | 0 | 0 | 0 |
| Grapefruit essential oil | 0 | 0 | 0 | 0 | 0 |
| Lavender (*Lavendula angustifolium*) essential oil | 0 | 0 | 0 | 0 | 0 |
| Lemon essential oil | 4.99 | 4.99 | 4.99 | 4.99 | 0 |

To prepare the candles of Examples 19-22, Part A ingredients were weighed into a vessel and heated at 80° C. until the mixture was liquid. Part B was added to Part A and mixed for 2 minutes. Part A/B was removed from the heat and Part C was added. While the mixture was still liquid, the candle was poured into a container and a wick with a metal tab base was inserted into the center of the mixture. The completed candle was allowed to cool to room temperature. Formulation 26 was allowed to cool to 65° C. before pouring into the candle mold. Candles 23-26 were poured into small tea light candle sizes.

To prepare the candle of Example 23, Part B was mixed by hand and set aside. Part A ingredients were weighed into a vessel and heated at 80° C. until the mixture was liquid. The pre-mix of Part B was added to Part A and mixed together for 2 minutes. Part A/B was removed from the heat and Part C was added. The mixture was cooled to 65° C. and then poured into a container and a wick with a metal tab base was inserted into the center of the mixture. The completed candle was allowed to cool to room temperature.

Dipped taper candles can be prepared by repeatedly dipping a wick into molten candle formulation to build up a thick wax coating on the wick.

All poured candles developed a single crack near the wick upon cooling, except for candle 25, which showed no signs of cracking. Cracking is a known problem in the art, particularly with vegetable oil based waxes (see, for example, U.S. Pat. No. 6,503,285) and can generally be mitigated with wax choice, wax blends, cooling rate, additives, and other formulation aspects known in the art. All of the colored candles showed signs of pigment settling on the bottom of the container candle. Candle 27 exhibited a deeper red color indicative of better pigment incorporation by premixing the pigment with the ketal. The method of candle 27 can be used in conjunction with a fragrance to make a scented candle.

Example 24

Coating Formulations

Coating formulations were made using a Cowles blade on an overhead mixer as shown in the Tables below. The formulas below were made by adding the ingredients in order. The grind paste portion was made and put under shear until the proper dispersion was achieved of 7+ Hegman. Then the remaining ingredients were added to complete the formulation. The ingredients were loaded into the vessel and the Dupont Ti-pure 8960 Titanium Dioxide was loaded into the mixture slowly until the viscosity was uniform and the mixing solution made a donut upon mixing. After mixing for a period of time, an amount of the mixture was deposited on a Hegman grind block and a measurement of the dispersion was read. All of the systems had Hegman readings of 7.5 or better. Then the remaining ingredients were added to complete the formula.

Formula 24-1A-C- Polyester Melamine

| Comparative Example | Ingredient | 24-1A* Formula | 24-1B Formula | 24-1C |
|---|---|---|---|---|
| Saturated Polyester resin | Polymac 57-5789 | 45.73 | 45.73 | 45.73 |
| Melamine resin | Cymel 300 | 7.53 | 7.53 | 7.53 |
| Titanium Dioxide grind paste | Ti-pure R960 | 28.79 82.05 | 28.79 82.05 | 28.79 |
| Solvent | DPM acetate | 3.91 | 3.91 | 0 |
| Solvent | DBE | 3.91 | 0 | 0 |
| | Et-LPK | 0 | 3.91 | 7.82 |
| Hydrocarbon Solvent | BAS 150 | 7.73 | 7.73 | 7.73 |
| Catalyst | Nacure 1051 | 0.40 | 0.40 | 0.40 |
| Solvent | Optifilm 300 | 2.00 | 2.00 | 2.00 |
| Total | | 100.00 | 100.00 | 100.00 |

*Comparative Example

Formula 24-2A-B - 1K Polyester urethane

| Comparative Example | Ingredient | 24-2A* Formula | 24-2B |
|---|---|---|---|
| Polyester resin | Polymac HS57-5789 | 43.72 | 43.72 |
| Rheology additive | Aerosil 200 | 0.29 | 0.29 |
| Titanium Dioxide grind paste | Ti-pure R960 | 19.28 63.29 | 19.28 63.29 |
| Blocked isocyanate | Desmodur BL3175 | 1.95 | 1.95 |
| tin catalyst | Dabco T12 | 1.08 | 1.08 |
| epoxy resin | Epon 828 | 1.31 | 1.31 |
| Solvent | BAS 150 | 10.76 | 10.76 |
| Solvent | DBE | 8.37 | 0 |
| Solvent | Et-LPK | 0 | 8.37 |
| Solvent | Diacetone alcohol | 4.78 | 4.78 |
| Total | | 91.54 | 91.54 |

*Comparative

Formula 24-3A-B - 2K Polyester Urethane

| Comparative Example | Ingredient | 24-3A* Formula | 24-3BB Formula |
|---|---|---|---|
| PART A | | | |
| Acrylic resin | Joncryl 500 | 200.00 | 200.00 |
| Leveling agent | BYK 320 | 2.00 | 2.00 |
| Solvent | MAK | 40.00 | 0 |
| Solvent | Et-LPK | 0 | 40.00 |
| Pigment | Ti-Pure R-960 | 329.00 | 329.00 |
| Grind paste | | | |
| Acrylic resin | Joncryl 500 | 199.60 | 199.60 |
| Solvent | MAK | 116.10 | 116.10 |
| tin catalyst | Dabco T12 | 0.23 | 0.23 |
| Subtotal | | 886.93 | 886.93 |
| PART B | | 3B | 3B |
| Aliphatic isocyanate | Desmodur N3300 | 152.60 | 152.60 |
| Solvent | MAK | 29.20 | 29.20 |
| Total | | 1068.73 | 1068.73 |

*Comparative

After allowing the formulations to set overnight, observations were made regarding the material stability. All formulas showed minimal separation that was easy to mix to uniformity. Using a drawdown bar over steel Q-panels, film thicknesses of 1 and 3 mils were made using each of the formulations. The panels were put into a 175° C. oven for 30 minutes. The final film was evaluated for appearance, cross-hatch adhesion, and Methyl Ethyl Ketone double rubs. The cross-hatch adhesion was carried out per ASTM D3359 and the MEK double rubs was carried out per ASTM method D5402-06. The double rubs were performed using a rag that was soaked with MEK and then the number of double rubs was counted to see the effects on the coating. If the coating was worn away to the substrate, the testing was discontinued and number was reported. The cross-hatch adhesion test used Staples clear packing tape versus the type specified in ASTMD3359.

| Ex. | Et-LPK (%) | 1 mil Visual Appearance | MEK DR | Cross-hatch Adhesion | 3 mil Visual Appearance | MEK DR | Cross-hatch Adhesion |
|---|---|---|---|---|---|---|---|
| 24-1A | 0 | High gloss/grainy | 40 breakthrough | 5B | High gloss/grainy | 100 no mar | 5B |
| 24-1B | 3.91 | High gloss/grainy | 60 breakthrough | 5B | High gloss/grainy | 100 no mar | 5B |
| 24-1C | 7.82 | High gloss/grainy | 100 no mar | 5B | High gloss/grainy | 100 no mar | 5B |
| 24-2A | 0 | dull gloss/smooth | 3 breakthrough | 5B | dull gloss/smooth | 6 breakthrough | 5B |
| 24-2B | 9.14 | dull gloss/smooth | 3 breakthrough | 5B | dull gloss/smooth | 6 breakthrough | 5B |
| 24-3A | 0 | High gloss/smooth | 100 no mar | 5B | High gloss/smooth | 100 no mar | 5B |
| 24-3B | 3.74 | High gloss/smooth | 100 no mar | 5B | High gloss/smooth | 100 no mar | 5B |

Results showed that the Et-LPK showed increased cure/solvent resistance in the polyester melamine system. All other systems showed comparable results to the control solvent.

The following Formulation Examples illustrate specific possible formulations for the manufacture of cosmetic and other personal care formulations using the alkyl ketal esters of structure I. In particular, the alkyl ketal ester is methyl-LGK, ethyl-LGK, n-propyl-LGK, n-butyl-LGK, ethyl-LPK, n-butyl-LPK, ethyl-LEK, methyl-AcAcGK, ethyl-AcAcGK, ethyl-LTMEK, and ethyl-LTMPK. In a specific embodiment, the alkyl ketal ester is ethyl-LGK, ethyl-LPK, n-butyl-LGK, or a combination comprising at least one of the foregoing alkyl ketal esters.

TABLE 14

| | Lipstick. | |
|---|---|---|
| | Ingredient | weight % |
| Part A | Caprylic/Capric Triglyceride | 8.56 |
| | Octyldodecyl Stearoyl Stearate | 13.37 |
| | Triisostearyl Citrate | 4.05 |
| | Pentaerythrityl Tetraisostearate | 5.60 |
| | Jojoba Esters | 1.72 |
| | Lanolin Oil | 1.62 |
| | Bis-Diglyceryl Polyacyladipate-2 | 1.02 |
| | *Ricinus Communis* (Castor) Seed Oil | 20.50 |
| | *Copernicia Cerifera* (Carnauba) Wax | 2.30 |
| | *Euphorbia Cerifera* (Candelilla) Wax | 5.24 |
| | Cera Alba (Beeswax) | 2.09 |
| | Ozokerite Wax | 1.80 |
| | Microcrystalline Wax | 1.13 |
| | Phenoxyethanol | 1.00 |
| | Polyethylene | 1.00 |
| | Octyl Methoxycinnamate | 0.60 |
| | Tocopheryl Acetate | 0.05 |

TABLE 14-continued

| | Lipstick. | |
|---|---|---|
| | Ingredient | weight % |
| Part B | *Ricinus Communis* (Castor) Seed Oil | 10.00 |
| | D&C Red No. 6 Barium Lake | 6.25 |
| | Iron Oxide | 0.10 |
| | Alkyl ketal ester* | 12 |

*Alkyl keta ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the lipstick, weigh Part A and begin heating to 80-85° C. with mixing. Pregrind Part B. When Part A is completely melted and clear, add Part B color grind to Part a wax/oil mixture. When all the color is dispersed and the batch is uniform, pour into molds.

TABLE 15

| | Solid Lip Gloss. | |
|---|---|---|
| | Ingredient | weight % |
| Part A | Castor oil | 36.4 |
| | Ketal* | 10 |
| | Polyisobutene 250 | 30 |
| | Bees wax | 10 |
| | Candelila wax | 9 |
| | Mica pigment | 3 |
| Part B | Vitamin E acetate | 1 |
| | BHT | 0.2 |
| | Food flavoring | 0.4 |

*Alkyl keta ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the lip gloss, add Part A into a vessel and heat to 75° C. to melt wax, mixing until uniform. Remove from heat and add Part B, stirring well. While still liquid, pour into cosmetic container.

TABLE 16

| | Lip Balm. | |
|---|---|---|
| | Ingredient | weight % |
| Part A | Fractionated coconut oil | 13 |
| | Ketal | 10 |
| | Castor oil | 15 |
| | Triglyceride | 23 |
| | Shea butter | 12 |
| | Bees wax | 17 |
| | Lecithin | 1 |
| Part B | Titanium dioxide (optional: nano-sized) | 2 |
| | Alkyl ketal ester* | 4.8 |

TABLE 16-continued

Lip Balm.

| | Ingredient | weight % |
|---|---|---|
| Part C | Provitamin B5 | 1 |
| | Vitamin E acetate | 0.1 |
| | Vitamin E Tocopherol | 0.1 |
| | Allantoin | 0.2 |
| | Paraben-DU** | 0.5 |
| | Food flavoring | 0.3 |

*Alkyl keta ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the lip balm, pre-grind or pre-mix the ingredients of Part C. Add Part A to vessel and heat to 65 C until wax and butter are melted. Slowly add in Part C with mixing and mix until well dispersed. Remove from heat. Add ingredients of Part C to Parts A/B one by one and make sure the formulation is well mixed. Fill into molds while the formulation is still liquid. Allow to cool.

TABLE 17

Pressed Powder Eye Shadow "Nude Glitter"

| | Ingredient | weight % |
|---|---|---|
| Part A | Alkyl ketal ester* | 4 |
| | Cyclodimethicone | 3 |
| | Polyglyceryl oleate | 0.75 |
| | Vitamin E acetate | 1 |
| Part B | Pearl white mica | 31 |
| | Mica spheres (powder base) | 20 |
| | Talc powder (powder base) | 20 |
| | Beige mica | 5 |
| | Magnesium stearate | 5 |
| | Bismuth oxychloride (powder base) | 5 |
| | Titanium dioxide | 5 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the eyeshadow, combine the titanium dioxide and the pearl white mica in a mortar, stir very well and thoroughly with the pestle until the color is uniform. Add then the other ingredients of Part B, one after another, mixing well after each addition. Then add Part A to the mortar and blend well, for several minutes or until the ingredients are mixed and the color looks uniform. Fill the eye shadow into an eye shadow jar and press it with a suitable tool into eye shadow containers.

TABLE 18

Poured Velvet Eyeshadow

| | Ingredient | weight % |
|---|---|---|
| Part A | Isostearyl neopentanoate | 25 |
| | Alkyl ketal ester* | 25 |
| | Isononyl isononanoate, polybutene, pentaerythrityl tetraisostearate, and isostearyl alcohol | 4 |
| | Ethylhexyl hydroxystearate, triethylhexyl trimellitates, and C30-45 olefin | 11 |
| Part B | Methyl methacrylate crosspolymer | 14 |
| Part C | CI 77491, mica, and triethoxycaprylylsilane | 20 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the eyeshadow, heat Part A to 70 C until melted. Add Part B to Part A with stirring at 70° C. Add Part C to the combined Part A/B with stirring at 70° C. Pour into molds.

TABLE 19

Black Mascara.

| | Ingredient | weight % |
|---|---|---|
| Part A | Distilled Water | 68.4% |
| | Xanthan Gum | 0.2% |
| | Provitamin B5 | 0.5% |
| | Sorbitol or Glycerin | 2% |
| | Gum Arabic | 2% |
| Part B | Stearic Acid | 5% |
| | Candelilla Wax | 1.5% |
| | Ceteareth-20 | 1.7% |
| | Bees Wax | 4.5% |
| | Carnauba Wax | 2.7% |
| Part C | Iron Oxide Black | 10% |
| | Alkyl ketal ester* | 0.5% |
| Part D | Paraben-DU** | 1% |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the mascara, add Part A into a disinfected glass beaker and mix well until everything is dissolved. Add Part B into another disinfected glass beaker and heat to 75° C. Mix Part C well with mortar and pestle. When Part B is melted, add Part C and stir until the pigment is well dispersed. Heat Part A to the same temperature as Part B. Add the hot Part A slowly while stirring to hot Part B maintaining a temperature of 70° C. until the two ingredients are fully mixed. When the temperature has dropped below 60° C. add Part D and stir. While still hot and liquid, fill into mascara containers by using a pipette.

TABLE 20

Anhydrous Mascara

| | Ingredient | weight % |
|---|---|---|
| Part A | Alkyl ketal ester* | 30.95 |
| | AC polyethylene 6a wax | 11 |
| | Candelilla wax | 4.5 |
| | Hydroxylated lanolin | 0.25 |
| Part B | pentaerythrityl rosinate | 2 |
| | C9-11 isoparaffin | 2 |
| Part C | methylparaben | 0.2 |
| | propylparaben | 0.1 |
| Part D | zinc stearate | 1 |
| Part E | silica silylate | 1 |
| Part F | Petroleum distillates, quaternium-18 hectorite, propylene carbonate | 35 |
| Part G | black iron oxide | 12 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the mascara, prepare Part B in advance by stirring in a sealed vessel until dissolved. In a separate closed vessel, combine the ingredients of Part A and heat to 90-95° C. with stirring. When Part A is clear and well-mixed, add Part B and Part C, stirring until dissolved. Add Parts D through F in sequential order, mixing well with high shear after each addition.

TABLE 21

Gel Eyeliner

| | Ingredient | weight % |
|---|---|---|
| Part A | Distilled Water | 70% |
| Part B | Alkyl Ketal Ester* | 7% |
| | Candelilla Wax | 5% |

TABLE 21-continued

Gel Eyeliner

| | Ingredient | weight % |
|---|---|---|
| | Polyglucose | 1% |
| | Iron Oxide Black | 11% |
| | Microcrystalline Wax | 2% |
| | GelMaker EMU** | 3% |
| Part C | Phenoxyethanol-SA | 1% |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK
**GelMaker EMU - pre-mixed gelling system (Sodium acrylate/acryloyldimethyl taurate copolymer/isohexadecane/polysorbate 80).

To manufacture the eyeliner, add Part A into a heat resistant vessels and heat to 167° F. (75° C.). Add Part B to a heat resistant glass jar and heat to the same temperature. When Part B is fully melted, add Part A to Part B, while stirring well. Remove from the heat but continue stirring until the mixture is a homogenous gel. If more thickness is needed, add more GelMaker EMU. Add Part C to Part A/B and stir again well. Package into small jars or into lip liner applicators by using a syringe

TABLE 22

Long Wearing Eyeliner/Eye Shadow Stick

| Ingredient | weight % |
|---|---|
| Carnauba wax | 4.5 |
| Ceresin | 12 |
| Ethyl hexyl palmitate | 6.5 |
| Alkyl ketal ester* | 5 |
| Polyglyceryl-3-diisostearate | 0.5 |
| Methylparaben | 0.2 |
| Propylparaben | 0.1 |
| Manganese violet | 5.5 |
| Ultramarine blue | 5.5 |
| Bismuth oxychloride | 20 |
| Silica silylate | 1 |
| Cyclomethicone | 39.2 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the eyeliner/eyeshadow, combine the waxes and oils in a sealed high speed mixer. Heat to 85-90° C. until waxes are dissolved. Add pigments. Agitate until no undispersed pigments remain. Fill at 70-75° C. using hermetically sealed equipment.

TABLE 23

Colored Pencil

| | Ingredient | weight % |
|---|---|---|
| Part A | Ethyl cellulose | 1.5 |
| | Isostearyl alcohol | 5.9 |
| | Stearyl alcohol | 5.9 |
| Part B | Hydrogenated vegetable oil | 6.7 |
| | Paraffin | 6.7 |
| Part C | Colorants | 33.3 |
| | Alkyl ketal ester* | 5 |
| Part D | Cyclomethicone | 35 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the pencil, mix Part A and heat at 65-90° C. with stirring until everything dissolves. Maintain temperature of Part A. In a separate vessel, mix Part B and melt. Add molten Part B to hot Part A. Mix Part C and add to Parts A/B. Homogenize mixture and then mix in Part D. Pour mixture into a mold to cool. Remove the pencil from mold when solidified and cooled.

TABLE 24

Cream Blush

| | Ingredient | Weight % |
|---|---|---|
| Part A | Triglyceride (emollient) | 22.8% |
| | Alkyl ketal ester* | 15% |
| | Meadowfoam seed oil (emollient) | 10% |
| | Shea butter (emollient) | 3% |
| | Polyglyceryl oleate (emulsifier) | 2% |
| | Stearyl palmitate (thickener) | 3% |
| | Carnauba wax (thickener) | 2% |
| | Vitamin E tocopherol (antioxidant) | 0.2% |
| Part B | Kaolin (texturizer) | 7% |
| | Corn Starch AS (texturizer) | 10% |
| | Mica Spheres (texturizer) | 12% |
| | Pearl white Mica (color) | 4% |
| Part C | Mica Red (color) | 8% |
| | Phenoxyethanol/SA (preservative) | 1% |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the blush, add Part A into a disinfected glass beaker and heat to 176° F./80° C. to melt the ingredients. Add Part B to Part A and stir well. Then add Part C to Part A/B and stir again well. Remove from the heat and pour into a compact case or small pot containers and let cool. Color can be adjusted through the pigment choice and level. Consistency can be adjusted by changing stearyl palmitate and ketal levels.

TABLE 25

Powder Cream Blush

| | Ingredient | weight % |
|---|---|---|
| Part A | PPG-3 benzyl ether myristate | 38 |
| | Tribehenin | 6 |
| | C18-36 acid triglyceride | 1 |
| | Sorbitan isostearate | 1 |
| | Methyl paraben | 0.2 |
| | Propyl paraben | 0.1 |
| Part B | D&C Red #6 Lake | 0.1 |
| | D&C Red #7 Lake | 0.1 |
| | AS 5126 Red Iron oxide color techniques | 0.9 |
| | AS 5146 Black Iron oxide color techniques | 0.2 |
| | Alkyl ketal ester* | 2 |
| Part C | AS Duan Talc 50707 Color techniques | 20.4 |
| | Mica AS Sericite 5061 Color techniques | 14 |
| | Bismuth oxychloride | 16 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the blush, add part A to vessel and heat at 75-80° C. with stirring until clear. In a separate vessel, blend part B and pass over a 3 roll-mill until particle size is 20 micrometers. Add Part B to Part A and stir until smooth and pigments are wetted. Maintain temperature at 75-80° C. Add Part C and mix at high speed until homogeneous. Allow to de-air while hot and then pour into pans.

TABLE 26

Oil in Water Foundation

| | Ingredient | weight % | Function |
|---|---|---|---|
| Part A | DI water | 50.92 | Diluents |
| | tromethamine | 0.8 | alkali (soap) |
| | PEG-12 dimethicone | 0.1 | wetting agent |
| | 80% TiO2/talc extender | 8 | Pigment |
| | 80% yellow iron oxide/talc ext. | 0.95 | Pigment |
| | 80% red iron oxide/talc ext | 0.75 | Pigment |
| | 80% black iron oxide/talc ext. | 0.07 | Pigment |
| | talc, average 4 micron | 4.23 | Filler |
| Part B | butylene glycol | 4 | Humectants |
| | magnesium aluminum silicate | 1 | Thickener |
| Part C | butylene glycol | 2 | Humectants |
| | cellulose gum | 0.15 | Thickener |
| Part D | sucrose cocate | 1 | Emulsifier |
| | methyl paraben | 0.2 | Preservative |
| | disodium EDTA | 0.05 | preservative aid |
| Part E | stearic acid | 1.5 | acid portion of soap |
| | isostearic acid | 0.5 | Soap |
| | dicaprylyl maleate | 10 | Emollient |
| | Alkyl ketal ester* | 6 | Emollient |
| | sorbitol monolaurate | 3 | Emulsifier |
| | cetyl alcohol | 0.5 | Stabilizer |
| | propyl paraben | 1 | Preservative |
| Part F | cyclomethicone | 2 | volatile emollient |
| Part G | DI water | 2 | Diluents |
| | DMDM hydantoin | 0.1 | Preservative |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the foundation, combine Part A ingredients in order while homogenizing. Combine and add Part B. Heat to 85-90° C. for 15 minutes and then cool to 75° C. Combine and add Part C. Add Part D ingredients in order. Combine ingredients of Part E and heat to 75-80° C. with stirring. Just prior to emulsification, add Part F and readjust temperature to 75-80° C. Add oil phase (combined Parts E and F) to water phase (combined Parts A-D) while homogenizing. Maintain temperature and agitation for at least 15 minutes. Cool to 55° C. and check for water loss. Cool to 45° C. with paddle mixer. Combine ingredients of Part G and add to the formulation. Cool to 30° C. and remove from heat.

TABLE 28

Foundation

| | Ingredient | weight % |
|---|---|---|
| Part A | DI water | 50 |
| | Potassium hydroxide (10% aq. solution) | 1.3 |
| | Polysorbate 80 | 0.1 |
| | Alkyl ketal ester* | 4.33 |
| Part B | Titanium dioxide | 7 |
| | Talc | 3.76 |
| | Yellow iron oxide | 0.8 |
| | Red iron oxide | 0.36 |
| | Black iron oxide | 0.09 |
| Part C | Propylene glycol | 2 |
| | Magnesium aluminum silicate | 1 |
| Part D | Propylene glycol | 4 |
| | Cellulose gum | 0.12 |
| Part E | Di-ppg-3 Myristyl ether adipate | 12 |
| | Alkyl ketal ester* | 4 |
| | Cetearyl alcohol, ceteth-20 phosphate, dicetyl phosphate | 3 |
| | Steareth-10 | 2 |
| | Cetyl alcohol | 0.62 |
| | Steareth-2 | 0.50 |
| Part F | Paraben-DU** | 1 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the foundation, combine Part A and begin homogenizing. Pre-mill Part B until pigments are well blended. Add Part B to Part A and homogenize until pigments are evenly dispersed. Begin heating A/B. Prepare a slurry of Part C and add to Parts A/B and heat to 85° C., maintaining temperature in the 85-90° C. range for 10 minutes. Remove from heat and prepare a second slurry of the ingredients in Part D. Add the slurried of Part D to A/B/C at 77° C. Homogenize until uniform and smooth. Check weight and add water to compensate for any loss, plus another 20 g/kg of formulation. Continue mixing and increase temperature to 77 C. Combine Part E ingredients separately and heat to 77° C. Add to main mixture and maintain temperature at 77-80° C. for 10 minutes. Remove from heat. Add Part F when the mixture has cooled to 50° C. Check for water loss and adjust formulation accordingly. Adjust pH to 7.5 if necessary. Homogenize until temperature reaches 35° C.

In a variation, one of the alkyl ketal esters is a blend of Et-LGK and an alkyl ketal ester of Exs. B-K.

TABLE 29

Concealer Stick

| | Ingredient | weight % |
|---|---|---|
| Part A | Titanium dioxide (A-8112) | 20 |
| | Red iron oxide (A-1301) | 1.4 |
| | Red Iron Oxide (A-1226) | 0.65 |
| | Black iron oxide (A-7133) | 0.1 |
| | Alkyl ketal ester* | 15.85 |
| | Di-PPG-3 Myristyl Ether Adipate | 4.25 |
| | Sorbitan Isostearate | 4.25 |
| Part B | Sericite AS | 10 |
| | Talc | 5 |
| | Di-PPG-3 Myristyl ether adipate | 2.5 |
| | Kaolin | 4 |
| Part C | Squalane | 3.5 |
| | Candelilla wax | 5 |
| | Ozokerite wax | 2.5 |
| | Propyl paraben | 0.1 |
| | Methyl paraben | 0.2 |
| | Carnauba wax | 1.75 |
| | C18-36 acid glycol ester | 2.25 |
| | C18-36 Acid Triglyceride | 1.1 |
| | Di-PPG-3 Myristyl ether Adipate | 14.6 |
| | DERMAXYL (from Croda) | 1 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the concealer, grind the ingredients of Part A and homogenize for at least 15 minutes. Add the ingredients of Part B to Part A and mix for at least 10 minutes. Combine all of the ingredients of Part C in a separate vessel and begin heating while mixing. Continue heating until batch becomes clear. Begin cooling while mixing and add Parts A/B to the batch. Pre-warm the stick molds and pour the batch into molds while the batch is still pourable. Allow molds to cool.

TABLE 30

Pressed Mineral Powder

| | Ingredient | weight % |
|---|---|---|
| Part A | Pigment blend (color of choice) | 3 |
| | Titanium dioxide | 3 |
| | Talc | 26 |
| | Bismuth oxychloride | 15 |
| | Magnesium stearate | 12 |
| | Micronized titanium dioxide | 6 |
| | Kaolin | 5.5 |
| | Zinc oxide | 2 |
| Part B | Alkyl ketal ester* | 3.5 |
| | Grapeseed oil | 2 |
| | Triglycerides | 2 |
| Part C | Mica spheres | 20 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the powder, mill Part A until it turns a uniform color. Add part B to Part A and mill again. Add Part C and blend for only a short time. Fill container and compress to form a solid.

TABLE 31

Loose Mineral Powder

| | Ingredient | weight % |
|---|---|---|
| Part A | Pigment blend (color of choice) | 3 |
| | Titanium dioxide | 5 |
| | Talc | 26 |
| | Bismuth oxychloride | 15 |
| | Magnesium stearate | 12 |
| | Micronized titanium dioxide | 7 |
| | Kaolin | 5.5 |
| | Zinc oxide | 3 |
| Part B | Alkyl ketal ester* | 3.5 |
| Part C | Mica spheres | 20 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK To manufacture the powder, mill Part A until it turns a uniform color. Add part B to Part A and mill again. Add Part C and blend for only a short time. Fill container. Do not compress.

TABLE 32

Baby Soft Diaper Rash Cream

| | Ingredient | weight % |
|---|---|---|
| Part A | Squalane | 30 |
| | Alkyl Ketal Ester* | 5 |
| | Zinc oxide | 12 |
| | CRODAFOS CES (cetearyl alcohol, dicetyl phosphate, and ceteth-10 phosphate) | 6 |
| Part B | Deionized water | 44.10 |
| | Methylparaben, butylparaben, ethylparaben, and propylparaben | 0.3 |
| Part C | Dimethicone | 0.6 |

*Alkyl ketal ester examples: Ex. A, methyl-LGK Ex. B, ethyl-LGK Ex. C, n-propyl-LGK Ex. D, n-butyl-LGK Ex. E, ethyl-LPK Ex. F, n-butyl-LPK Ex. G, ethyl-LEK Ex. H, Me-AcAcGK Ex. I, Et-AcAcGK Ex. J, ethyl-LTMEK Ex. K, ethyl-LTMPK The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The endpoints of all ranges directed to the same component or property are inclusive of the endpoint and independently combinable.

Unless otherwise defined, all terms (including technical and scientific terms) used herein have the same meaning as commonly understood by one of ordinary skill in the art to which this invention belongs.

The above-described compounds have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. Alkyl groups can be straight-chained or branched. Hydroxyl groups have the formula —OH.

As used herein, a "formulation" refers to both a composition that can be used to manufacture a product, and the product itself, i.e., in the form provided to the user. Compositions can be used to manufacture a product by addition of one or more additional ingredients and/or subjecting the formulation to one or more processing steps, including in some embodiments simply packaging the composition.

Further as used herein, unless indicated otherwise by context, an "alcohol" means a C1-7 alkanol such as methanol, ethanol, 1-propanol, 2-propanol, 1-butanol, 2-butanol, t-butanol, 1-pentanol, and 1-hexanol, as well as the various other isomers of pentanol and hexanol; alkylene glycols such as ethylene glycol, diethylene glycol, triethylene glycol, 1,2-propylene glycol, 1,3-propane diol, dipropylene glycol, tripropylene glycol 1,4-butane diol and 1,2-butane diol; triols such as glycerine, and the like. In an embodiment, an alcohol is methanol, ethanol, 1-propanol, 2-propanol, 1-butanol, 2-butanol, t-butanol, 1-pentanol, 1-hexanol, ethylene glycol, 1,2-propylene glycol, and 1,3-propane diol.

All cited patents, patent applications, and other references are incorporated herein by reference in their entirety.

The various embodiments described are provided by way of illustration only and should not be construed to limit the claims attached hereto. The present invention can suitably comprise, consist of, or consist essentially of, any of the disclosed or recited elements. Thus, the invention illustratively disclosed herein can be suitably practiced in the absence of any element, which is not specifically disclosed herein. Various modifications and changes will be recognized that can be made without following the example embodiments and applications illustrated and described herein, and without departing from the true spirit and scope of the following claims.

What is claimed is:
1. A dispersion comprising
    a liquid or semi-solid continuous phase,
    a dispersed solid phase comprising a plurality of organic, inorganic or inorganic-organic particles, and
    an alkyl ketal ester having the structure

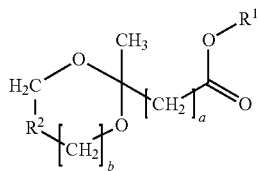

wherein
a is 0 or an integer of 1 to 12;
b is 0 or 1;
$R^2$ is a divalent $C_{1-8}$ group optionally substituted with up to 5 hydroxyl groups; and
$R^1$ is $C_{1-6}$ alkyl, and
wherein at least a portion of the alkyl ketal ester is present in the continuous phase, on a surface of at least some of the dispersed particles, or a combination thereof.

2. The dispersion of claim 1, wherein $R^2$ is >CH—CH$_3$, >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH.

3. The dispersion of claim 1, wherein the alkyl ketal ester is selected from ethyl-LGK, ethyl-LPK, n-butyl-LGK, n-butyl-LPK, and combinations thereof.

4. A coating composition comprising the dispersion of claim 1, wherein
the continuous phase is a liquid continuous phase, and
the plurality of solid particles comprises solid pigment particles.

5. The coating composition of claim 4, wherein the alkyl ketal ester is present in the dispersion in an amount from 1 to 400% by weight of plurality of solid particles.

6. The coating composition of claim 4, wherein the dispersed pigment particles have an average D50 particle size from 100 nanometers to 25 micrometers.

7. The coating composition of claim 4, comprising, based on the total weight of the coating composition,
from 20 to 90% by weight of the liquid continuous phase,
from 0.5 to 45% by weight of the solid pigment particles,
from 0.5 to 60% by weight of the alkyl ketal ester, and
from 5 to 80% by weight of an organic binder composition.

8. The dispersion of claim 1, wherein the continuous phase is a semi-solid.

9. The dispersion of claim 8, wherein the semi-solid is a wax.

10. A cosmetic comprising the dispersion of claim 1, wherein
the continuous phase comprises a cosmetically acceptable wax, film-forming polymer, emollient, or a combination thereof, and
the plurality of solid particles comprises cosmetically acceptable solid pigment particles.

11. The cosmetic of claim 10, in the form of a semi-solid, comprising, based on the total weight of the cosmetic,
from 25 to 80% by weight of the continuous phase,
from 5 to 50% by weight of the solid pigment particles, and
from 0.1 to 50% of the weight of the alkyl ketal ester.

12. The cosmetic of claim 11, wherein the cosmetic is an eye product, skin product, lip product, or nail product.

13. The cosmetic of claim 10, in the form of a fluid or gel, comprising, based on the total weight of the cosmetic,
from 25 to 80% by weight of water, a volatile organic solvent, or a combination thereof,
from 2 to 35% of the cosmetically acceptable wax, film-forming polymer, emollient, or combination thereof,
from 2 to 30% by weight of the solid pigment particles, and
from 1 to 40% by weight of the alkyl ketal ester.

14. The cosmetic of claim 13, wherein the cosmetic is an eye product, lip product, skin product or nail product.

15. The cosmetic of claim 10, in the form of a wet foundation comprising, based on the total weight of the cosmetic,
from 30-75% by weight water,
from 1 to 35% by weight of the cosmetically acceptable emollient, from 2 to 25% by weight of the solid pigment particles, and
from 0.5 to 35% by weight of the alkyl ketal ester, wherein the continuous phase is an aqueous phase or an oily phase.

16. The cosmetic of claim 10, in the form of a lip product comprising, based on the total weight of the cosmetic,
from 1 to 25% by weight of the cosmetically acceptable wax;
from 30 to 95% by weight of one or more other hydrophobic materials; and
from 0.05 to 25% by weight of the solid pigment particles.

17. A composition, comprising
a plurality of solid particles; and
an alkyl ketal ester at least partially coating at least some of the particles, the alkyl ketal ester having the structure:

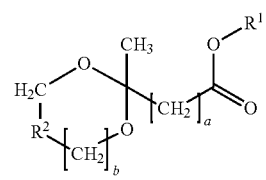

wherein
a is 0 or an integer of 1 to 12;
b is 0 or 1;
$R^2$ is a divalent $C_{1-8}$ group optionally substituted with up to 5 hydroxyl groups; and
$R^1$ is $C_{1-6}$ alkyl; and
wherein the composition is a particulate solid.

18. The composition of claim 17, wherein $R^2$ is >CH—CH$_3$, >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH.

19. The composition of claim 17, wherein the alkyl ketal ester is selected from ethyl-LGK, ethyl-LPK, n-butyl-LGK, n-butyl-LPK, and combinations thereof.

20. The composition of claim 17 wherein the alkyl ketal ester is present in an amount from 1 to 100% by weight of the plurality of solid particles.

21. The composition of claim 17, wherein the plurality of solid particles comprise pigment particles, and the alkyl ketal ester is sorbed onto at least a portion of a surface of at least a portion of the pigment particles.

22. A powder cosmetic comprising the composition of claim 17, and comprising, based on the total weight of the powder cosmetic, from 50 to 95% by weight of the solid pigment particles, and from 1 to 15% by weight of the alkyl ketal ester.

23. A method of forming the dispersion of claim 1, comprising combining the continuous phase, plurality of solid particles, and alkyl ketal ester to form the dispersion.

24. The method of claim 23, wherein the combining comprises wetting the plurality of solid particles with the alkyl ketal ester; then combining the wetted particles with the continuous phase.

25. The method of claim 23, wherein the combining comprises combining the continuous phase and the alkyl ketal ester; and adding the plurality of solid particles to the combination of the continuous phase and the alkyl ketal ester.

\* \* \* \* \*